US007592455B2

(12) United States Patent
Brookings et al.

(10) Patent No.: US 7,592,455 B2
(45) Date of Patent: *Sep. 22, 2009

(54) BICYCLIC HETEROAROMATIC COMPOUNDS AS KINASE INHIBITORS

(75) Inventors: Daniel Christopher Brookings, Reading (GB); Jeremy Martin Davis, Wokingham (GB); Barry John Langham, Reading (GB)

(73) Assignee: UCB Pharma S.A., Brussels (BE)

( * ) Notice: Subject to any disclaimer, the term of this patent is extended or adjusted under 35 U.S.C. 154(b) by 505 days.

This patent is subject to a terminal disclaimer.

(21) Appl. No.: 10/524,199

(22) PCT Filed: Aug. 11, 2003

(86) PCT No.: PCT/GB03/03501

§ 371 (c)(1),
(2), (4) Date: Jul. 28, 2005

(87) PCT Pub. No.: WO2004/014920

PCT Pub. Date: Feb. 19, 2004

(65) Prior Publication Data

US 2006/0025428 A1 Feb. 2, 2006

(30) Foreign Application Priority Data

Aug. 13, 2002 (GB) ................................ 0218800.1

(51) Int. Cl.
*C07D 513/02* (2006.01)
(52) U.S. Cl. .................................................. 546/114
(58) Field of Classification Search .................. 546/114
See application file for complete search history.

(56) References Cited

U.S. PATENT DOCUMENTS

| 3,935,222 | A | 1/1976 | Hoehn .................. 260/295.5 B |
| 6,169,092 | B1 | 1/2001 | Bräunlich et al. ............. 514/258 |
| 6,180,792 | B1 * | 1/2001 | Furuya et al. ................ 544/278 |
| 6,949,651 | B2 * | 9/2005 | Wilson ........................ 546/114 |
| 2006/0004025 | A1 | 1/2006 | Brookings et al. |
| 2006/0247269 | A1 | 11/2006 | Brookings et al. |
| 2007/0078131 | A1 | 4/2007 | Alexander |
| 2007/0099894 | A1 | 5/2007 | Langham |

FOREIGN PATENT DOCUMENTS

| WO | WO 99/64400 A1 | 12/1999 |
| WO | WO 03/033502 A1 | 4/2003 |
| WO | WO 03033502 | * 4/2003 |

OTHER PUBLICATIONS

Litvinov et al. STN Accession No. 1984:630317 Document No. 101:230317 Abstract of Izvestiya Akademii Nauk SSSR, Seriya Khimicheskaya (1984), (8), 1869-70.*

Dotsenko eta l. Russian Accession No. 2002:851387 Document No. 138:337962 Abstract of Chemical Bulletin (Translation of Izvestiya Akademii Nauk, Seriya Khimicheskaya) (2002), 51(8), 1556-1561.*

Adams, J.L., et al., "p38 MAP kinase: molecular target for the inhibition of pro-inflammatory cytokines," *Progress in Medicinal Chem.*, Elsevier Science, King, F.D., et al. (Eds.), 2001, 38, 1-60.

Adhikari, R., et al., "An adventitious synthesis of 2,2'-dipyrryl disulfides," *Aust. J. Chem.*, 1999, 52, 63-67.

Allen, M., et al., "Deficiency of the stress kinase p38α results in embryonic lethality: characterization of the kinase dependence of stress responses of enzyme-deficient embryonic stem cells," *J. Exp. Med.*, 2000, 191, 859-869.

Badger, A.M., et al., "Pharmacological profile of SB 203580, a selective inhibitor of cytokine suppressive binding protein/p38 kinase, in animal models of arthritis, bone resorption, endotoxin shock and immune function," *J. Pharmacol. Exp. Ther.*, 1996, 279, 1453-1461.

Chan, D.T., et al., "New N- and O-arylations with phenylboronic acids and cupric acetate," *Tetrahedron Lett.*, 1998, 39, 2933-2936.

Cohen, P., "The search for physiological substrates of MAP and SAP kinases in mammalian cells," *Trends Cell Biol*, 1997, 7, 353-361.

Dinarello, C.A., et al., "An update on human interleukin-1: from molecular biology to clinical relevance," *J. Clinical Immunology*, 1985, 5, 287-297.

Doza, Y.N., et al., "Activation of the MAP kinase homologue RK requires the phosphorylation of Thr-180 and Tyr-182 and both residues are phosphorylated in chemically stressed KB cells," *FEBS Letts.*, 1995, 364, 223-228.

Enslen, H., et al., "Selective activation of p38 mitogen-activated protein (MAP) kinase isoforms by the MAP kinase kinases MKK3 and MKK6," *J. Biol. Chem.*, 1998, 273, 1741-1748.

Griswold, D.E., et al., "Pharmacology of cytokine suppressive anti-inflammatory drug binding protein (CSBP), a novel stress-induced kinase," *Pharmacol. Comm.*, 1996, 7, 323-329.

Hale, K.K. et al., "Differential expression and activation of 938 mitogen-activated protein kinase α, β, γ, and δ in inflammatory cell lineages," *J. Immun.*, 1999, 162, 4246-4252.

Hartwig, J.F., et al., "Transition metal catalyzed synthesis of arylamines and aryl ethers from aryl halides and triflates: scope and mechanism," *Angew. Chem. In. Ed. Engl.*, 1998, 37, 2046-2067.

Hunter, T., et al. (Eds), "Protein kinase classification," *Methods in Enzymology, Academic Press*, San Diego, 1991, vol. 200, 3-39.

Jiang, Y., et al., "Characterization of the structure and function of a new mitogen-activated protein kinase (p38β)," *J. of Biological Chem.*, 1996, 271(30), 17920-17926.

Konno, K., et al., "Improved procedures for preparation of 2-pyridones and 2-hydroxymethylpyridines from pyridine N-oxides," *Heterocycles*, 1986, 24(8), 2169-2172.

Kotlyarov, A., et al., "MAPKAP kinase 2 is essential for LPS induced TNF-α biosynthesis," *Nature Cell Biol.*, 1999, 1, 94-97.

(Continued)

*Primary Examiner*—D. Margaret Seaman
*Assistant Examiner*—Nizal S Chandrakumar
(74) *Attorney, Agent, or Firm*—McDonnell Boehnen Hulbert & Berghoff LLP

(57) ABSTRACT

A series of 5-6 fused ring bicyclic heteroaromatic derivatives, based in particular on the 6-oxo-6,7-dihydrothieno[2,3-b]pyridine ring system, being inhibitors of p38 kinase, are accordingly of use in medicine, for example in the treatment and/or prevention of immune or inflammatory disorders.

6 Claims, No Drawings

OTHER PUBLICATIONS

Lam, P.Y.S., et al., "Copper-catalyzed general C—N and C—O bond cross-coupling with arylboronic acid," *Tetrahedron Lett.*, 2001, 3415-3418.

Lee, J.C., et al., "Bicyclic imidazoles as a novel class of cytokine biosynthesis inhibitors," *Annals N.Y. Acad. Sci.*, 1993, 696, 149-170.

Lee, J.C., et al., "Inhibition of monocyte IL-1 production by the anti-inflammatory compound, SKandP 86002," *Int. J. Immunopharm.*, 1988, 10(7), 835-843.

Lee, J.C., et al., "A protein kinase involved in the regulation of inflammatory cytokine biosynthesis," *Nature*, London, 1994, 372, 739-746.

Luker, T.J., et al., "Palladium catalysed amination of electron deficient halothiophenes," *Tetrah. Letts.*, 2000, 41, 7731-7735.

McDonnell, P.C., et al., "Localization of the human stress responsive MAP kinase-like CSAIDs binding protein gene to chromosome 6p21.3/21.2," *Genomics*, 1995, 29, 301-302.

Subauste, M.C., et al., "Infection of a human respiratory epithelial cell line with rhinovirus," *J. Clin. Invest.*, 1995, 96, 549-557.

Sont, J.K., et al., "Fully automated assessment of inflammatory cell counts and cytokine expression in bronchial tissue," *Am. J. Respir Crit. Care Med.*, 2003, 167, 1496-1503.

Takekawa, M., et al., "A family of stress-inducible GADD45-like proteins mediated activation of the stress-responsive MTK1/MEKK4 MAPKKK," *Cell*, 1998, 95, 521-530.

Teran, L.M., et al., "Role of nasal interleukin-8 in neutrophil recruitment and activation in children with virus-induced asthma," *Am. J. Respir. Crit. Care Med.*, 1997, 155, 1362-1366.

Turner, R.B., et al., "Association between interleukin-8 concentration in nasal secretions and severity of symptoms of experimental rhinovirus colds," *Clin. Infec. Dis.*, 1997, 26, 840-846.

Wolfe, J.P., et al., "Scope and limitations of the Pd/BINAP-catalyzed amination of aryl bromides," *J. Org. Chem.*, 2000, 65, 1144-1157.

Zhu, Z., et al., "Rhinovirus stimulation of interleukin-6 in vivo and in vitro," *J. Clin. Invest.*, 1996, 97(2), 421-430.

\* cited by examiner

BICYCLIC HETEROAROMATIC COMPOUNDS AS KINASE INHIBITORS

This invention relates to a series of 5-6 fused ring bicyclic heteroaromatic derivatives, to compositions containing them, to processes for their preparation and to their use in medicine.

Immune and inflammatory responses involve a variety of cell types with control and co-ordination of the various interactions occurring via both cell-cell contacts (e.g. integrin interactions with their receptors) and by way of intercellular signalling molecules. A large number of different signalling molecules are involved including cytokines, lymphocytes, chemokines and growth factors.

Cells respond to such intercellular signalling molecules by means of intracellular signalling mechanisms that include protein kinases, phosphatases and phospholipases. There are five classes of protein kinase of which the major ones are the tyrosine kinases and the serine/threonine kinases [Hunter, T., *Methods in Enzymology* (*Protein Kinase Classification*), p. 3, Hunter, T. and Sefton, B. M. eds., vol. 200, Academic Press, San Diego, 1991].

One sub-class of serine/threonine kinases is the mitogen activating protein (MAP) kinases of which there are at least three families which differ in the sequence and size of the activation loop [Adams, J. L. et al., *Progress in Medicinal Chemistry*, pp. 1-60, King, F. D. and Oxford, A. W. eds., vol. 38, Elsevier Science, 2001]: the extracellular regulated kinases (ERKs); the c-Jun $NH_2$ terminal kinases or stress activated kinases (JNKs or SAP kinases); and the p38 kinases, which have a threonine-glycine-tyrosine (TGY) activation motif. Both the JNKs and p38 MAP kinases are primarily activated by stress stimuli including, but not limited to, proinflammatory cytokines, e.g. tumour necrosis factor (TNF) and interleukin-1 (IL-1), ultraviolet light, endotoxin and chemical or osmotic shock.

Four isoforms of p38 have been described (p38α/β/γ/δ). The human p38 α enzyme was initially identified as a target of cytokine-suppressive anti-inflammatory drugs (CSAIDs) and the two isoenzymes found were initially termed CSAID binding protein-1 and -2 (CSBP-1 and CSBP-2 respectively) [Lee, J. C. et al., *Nature* (*London*), 1994, 372, 739-46]. CSBP-2 is now widely referred to as p38α and differs from CSBP-1 in an internal sequence of 25 amino acids as a result of differential splicing of two exons that are conserved in both mouse and human [McDonnell, P. C. et al., *Genomics*, 1995, 29,301-2]. CSBP-1 and p38α are expressed ubiquitously and there is no difference between the two isoforms with respect to tissue distribution, activation profile, substrate preference or CSAID binding. A second isoform is p38β which has 70% identity with p38α. A second form of p38β termed p38β2 is also known and of the two this is believed to be the major form. p38α and p38β2 are expressed in many different tissues. However, in monocytes and macrophages p38α is the predominant kinase activity [Lee, J. C., ibid; Jing, Y. et al., *J. Biol. Chem.*, 1996, 271, 10531-34; Hale, K. K. et al., *J. Immun.*, 1999, 162, 4246-52]. p38γ and p38δ (also termed SAP kinase-3 and SAP kinase-4 respectively) have ~63% and ~61% homology to p38α respectively. p38γ is predominantly expressed in skeletal muscle whilst p38δ is found in testes, pancreas, prostate, small intestine and in certain endocrine tissues.

All p38 homologues and splice variants contain a 12 amino acid activation loop that includes a Thr-Gly-Tyr motif. Dual phosphorylation of both Thr-180 and Tyr-182 in the TGY motif by a dual specificity upstream kinase is essential for the activation of p38 and results in a >1000-fold increase in specific activity of these enzymes [Doza, Y. N. et al., *FEBS Lett.*, 1995, 364, 7095-8012]. This dual phosphorylation is effected by MKK6 and, under certain conditions, the related enzyme MKK3 [Enslen, H. et al., *J. Biol. Chem.*, 1998, 273, 1741-48]. MKK3 and MKK6 belong to a family of enzymes termed MAPKK (mitogen activating protein kinase kinase) which are in turn activated by MAPKKK (mitogen activating kinase kinase kinase) otherwise known as MAP3K.

Several MAP3Ks have been identified that are activated by a wide variety of stimuli including environmental stress, inflammatory cytokines and other factors. MEKK4/MTK1 (MAP or ERK kinase kinase/MAP three kinase-1), ASK1 (apoptosis stimulated kinase) and TAK1 (TGF-β-activated kinase) are some of the enzymes identified as upstream activators of MAPKKs. MEKK4/MTK1 is thought to be activated by several GADD-45-like genes that are induced in response to environmental stimuli and which eventually lead to p38 activation [Takekawa, M. and Saito, H., *Cell*, 1998, 95, 521-30]. TAK1 has been shown to activate MKK6 in response to transforming growth factor-β (TGF-β). TNF-stimulated activation of p38 is believed to be mediated by the recruitment of TRAF2 (TNF receptor associated factor) and the Fas adaptor protein, Daxx, which results in the activation of ASK1 and subsequently p38.

Several substrates of p38 have been identified including other kinases [e.g. MAPK activated protein kinase 2/3/5 (IAPKAP 2/3/5), p38 regulated/activated protein kinase (PRAK), MAP linase-interacting kinase 1/2 (MNK1/2), mitogen- and stress-activated protein kinase 1 (MSK1/RLPK) and ribosomal S6 kinase-B (RSK-B)], transcription factors [e.g. activating transcription factor 2/6 (ATF2/6), monocyte-enhancer factor-2A/C (MEF2A/C), C/EBP homologous protein (CHOP), Elk1 and Sap-1a1] and other substrates [e.g. cPLA2, p47phox].

MAPKAP K2 is activated by p38 in response to environmental stress. Mice engineered to lack MAPKAP K2 do not produce TNF in response to lipopolysaccharide (LPS). Production of several other cytokines such as IL-1, IL-6, IFN-g and IL-10 is also partially inhibited [Kotlyarov, A. et al., *Nature Cell Biol.*, 1999, 1, 94-7]. Further, MAPKAP K2 from embryonic stem cells from p38α null mice was not activated in response to stress and these cells did not produce IL-6 in response to IL-1 [Allen, M. et al., *J. Exp. Med.*, 2000, 191, 859-69]. These results indicate that MAPKAP K2 is not only essential for TNF and IL-1 production but also for signalling induced by cytokines. In addition, MAPKAP K2/3 phosphorylate and thus regulate heat shock proteins HSP 25 and HSP 27 which are involved in cytoskeletal reorganization.

Several small molecule inhibitors of p38 have been reported which inhibit IL-1 and TNF synthesis in human monocytes at concentrations in the low μM range [Lee, J. C. et al, *Int. J. Immunopharm.*, 1988, 10, 835] and exhibit activity in animal models which are refractory to cyclooxygenase inhibitors [Lee, J. C. et al., *Annals N.Y. Acad. Sci.*, 1993, 696, 149]. In addition, these small molecule inhibitors are known to decrease the synthesis of a wide variety of pro-inflammatory proteins including IL-6, IL-8, granulocyte/macrophage colony-stimulating factor (GM-CSF) and cyclooxygenase-2 (COX-2). TNF-induced phosphorylation and activation of cytosolic PLA2, TNF-induced expression of VCAM-1 on endothelial cells and IL-1 stimulated synthesis of collagenase and stromelysin are also inhibited by such small molecule inhibitors of p38 [Cohen, P., *Trends Cell Biol.*, 1997, 7, 353-61].

A variety of cells including monocytes and macrophages produce TNF and IL-1. Excessive or unregulated TNF production is implicated in a number of disease states including Crohn's disease, ulcerative colitis, pyresis, rheumatoid arthritis, rheumatoid spondylitis, osteoarthritis, gouty arthritis and other arthritic conditions, toxic shock syndrome, endotoxic shock, sepsis, septic shock, gram negative sepsis, bone resorption diseases, reperfasion injury, graft vs. host reaction, allograft rejection, adult respiratory distress syndrome, chronic pulmonary inflammatory disease, silicosis, pulmonary sarcoidosis, cerebral malaria, scar tissue formation, keloid formation, fever and myalgias due to infection, such as influenza, cachexia secondary to acquired immune deficiency syndrome (AIDS), cachexia secondary to infection or malignancy, AIDS or AIDS related complex.

Excessive or unregulated IL-1 production has been implicated in rheumatoid arthritis, osteoarthritis, traumatic arthritis, rubella arthritis, acute synovitis, psoriatic arthritis, cachexia, Reiter's syndrome, endotoxemia, toxic shock syndrome, tuberculosis, atherosclerosis, muscle degeneration, and other acute or chronic inflammatory diseases such as the inflammatory reaction induced by endotoxin or inflammatory bowel disease. In addition, IL-1 has been linked to diabetes and pancreatic β cells [Dinarello, C. A., *J. Clinical Immunology,* 1985, 5, 287-97].

IL-8 is a chemotactic factor produced by various cell types including endothelial cells, mononuclear cells, fibroblasts and keratinocytes. IL-1, TNF and LPS all induce the production of IL-8 by endothelial cells. In vitro IL-8 has been shown to have a number of functions including being a chemoattractant for neutrophils, T-lymphocytes and basophils. IL-8 has also been shown to increase the surface expression of Mac-1 (CD11b/CD18) on neutrophils without de novo protein synthesis, which may contribute to increased adhesion of neutrophils to vascular endothelial cells. Many diseases are characterised by massive neutrophil infiltration. Histamine release from basophils (in both atopic and normal individuals) is induced by IL-8 as is lysozomal enzyme release and respiratory burst from neutrophils.

The central role of IL-1 and TNF together with other leukocyte-derived cytokines as important and critical inflammatory mediators is well documented. The inhibition of these cytokines has been shown or would be expected to be of benefit in controlling, alleviating or reducing many of these disease states.

The central position that p38 occupies within the cascade of signalling molecules mediating extracellular to intracellular signalling, and its influence over not only IL-1, TNF and IL-8 production but also the synthesis and/or action of other pro-inflammatory proteins (e.g. IL-6, GM-CSF, COX-2, collagenase and stromelysin), make it an attractive target for inhibition by small molecule inhibitors with the expectation that such inhibition would be a highly effective mechanism for regulating the excessive and destructive activation of the immune system. Such an expectation is supported by the potent and diverse anti-inflammatory activities described for p38 kinase inhibitors [Adams, ibid; Badger et al., *J. Pharmacol. Exp. Ther.,* 1996, 279, 1453-61; Griswold et al., *Pharmacol. Commun.,* 1996, 7, 323-29].

We have now found a group of compounds which are potent and selective inhibitors of p38 kinase (p38α, β, γ and δ) and the isoforms and splice variants thereof, especially p38α, p38β and p38β2. The compounds are thus of use in medicine, for example in the prophylaxis and treatment of immune or inflammatory disorders as described herein.

Thus, according to one aspect of the invention we provide a compound of formula (1):

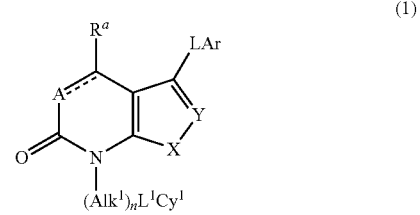

wherein the dashed line joining A and $C(R^a)$ is present and represents a bond and A is a —N= atom or a —$C(R^b)$= group, or the dashed line is absent and A is a —$N(R^b)$— or —$C(R^b)(R^c)$— group;

$R^a$, $R^b$ and $R^c$ is each independently a hydrogen atom or an optionally substituted $C_{1-6}$ alkyl, —CN, —$CO_2H$, —$CO_2R^1$ (where $R^1$ is an optionally substituted alkyl group), —$CONH_2$, —$CONHR^1$ or —$CONR^1R^2$ group (where $R^2$ is an optionally substituted alkyl group);

X is an —O—, —S— or substituted nitrogen atom or a —S(O)—, —$S(O)_2$— or —NH— group;

Y is a nitrogen or substituted carbon atom or a —CH= group;

n is zero or the integer 1;

$Alk^1$ is an optionally substituted aliphatic or heteroaliphatic chain;

$L^1$ is a covalent bond or a linker atom or group;

$Cy^1$ is a hydrogen atom or an optionally substituted cycloaliphatic, polycycloaliphatic, heterocycloaliphatic, polyheterocycloaliphatic, aromatic or heteroaromatic group;

L is an atom or chain —$(CH_2)_p$Het$(CH_2)_q$— in which p and q, which may be the same or different, is each zero or the integer 1 and Het is an —O— or —S— atom or a —$C(R^{3a})(R^{3b})$— (where $R^{3a}$ and $R^{3b}$, which may be the same or different, is each a hydrogen atom or an —OH or optionally substituted $C_{1-6}$ alkyl group), —C(O)—, —C(O)O—, —OC(O)—, —C(S)—, —S(O)—, —$S(O)_2$—, —$N(R^{3c})$O— (where $R^{3c}$ is a hydrogen atom or a straight or branched alkyl group), —$N(R^{3c})NH$—, —$N(R^{3c})C(R^{3a})(R^{3b})$—, —CON$(R^{3c})$—, —OC(O)N$(R^{3c})$—, —CSN$(R^{3c})$—, —$N(R^{3c})$CO—, —$N(R^{3c})C(O)O$—, —$N(R^{3c})CS$—, —$S(O)_2N(R^{3c})$—, —$N(R^{3c})S(O)_2$—, —$N(R^{3c})CON(R^{3d})$— (where $R^{3d}$ is as defined for $R^{3c}$ and may be the same or different), —$N(R^{3c})CSN(R^{3d})$— or —$N(R^{3c})S(O)_2NR^{3d}$— group and, when one or both of p and q is the integer 1, Het is additionally a —$N(R^{3c})$— group; and Ar is an optionally substituted aromatic or heteroaromatic group; and the salts, solvates, hydrates and N-oxides thereof.

The present invention also provides a compound of formula (1) as depicted above, or a salt, solvate, hydrate or N-oxide thereof, wherein L is other than —$N(R^{3c})C(R^{3a})(R^{3b})$—, and the remaining substituents are as defined above.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise. In addition, compounds of formula (1) may exist as tautomers, for example keto ($CH_2C$=O)-enol(CH=CHOH) tautomers.

Formula (1) and the formulae hereinafter are intended to represent all individual tautomers and mixtures thereof, unless stated otherwise.

As used in formula (1) the terms "substituted nitrogen atom" and "substituted carbon atom" are intended to include groups such as those in which X is —N($R^{10}$)— and Y is —C($R^{10}$)═ where $R^{10}$ is a substituent other than a hydrogen atom as generally or particularly defined hereinafter.

The following general terms as used herein in relation to compounds of the invention and intermediates thereto have the stated meaning below unless specifically defined otherwise.

Thus, as used herein, the term "alkyl" whether present as a group or part of a group includes straight or branched $C_{1-6}$ alkyl groups, for example $C_{1-4}$ alkyl groups such as methyl, ethyl, n-propyl, isopropyl, n-butyl, sec-butyl, isobutyl or tert-butyl groups. Similarly, the terms "alkenyl" and "alkynyl" are intended to mean straight or branched $C_{2-6}$ alkenyl or $C_{2-6}$ alkynyl groups such as $C_{2-4}$ alkenyl or $C_{2-4}$ alkynyl groups. Optional substituents which may be present on these groups include those optional substituents mentioned hereinafter in relation to $Alk^1$ when $Alk^1$ is an optionally substituted aliphatic chain.

The term halogen is intended to include fluorine, chlorine, bromine and iodine atoms.

The term "haloalkyl" is intended to include those alkyl groups just mentioned substituted by one, two or three of the halogen atoms just described. Particular examples of such groups include —$CF_3$, —$CCl_3$, —$CHF_2$, —$CHCl_2$, —$CH_2F$ and —$CH_2Cl$ groups.

The term "alkoxy" as used herein is intended to include straight or branched $C_{1-6}$ alkoxy, e.g. $C_{1-4}$ alkoxy such as methoxy, ethoxy, n-propoxy, isopropoxy, n-butoxy, sec-butoxy, isobutoxy and tert-butoxy. "Haloalkoxy" as used herein includes any of these alkoxy groups substituted by one, two or three halogen atoms as described above. Particular examples include —$OCF_3$, —$OCCl_3$, —$OCHF_2$, —$OCHCl_2$, —$OCH_2F$ and —$OCH_2Cl$ groups.

As used herein, the term "alkylthio" is intended to include straight or branched $C_{1-6}$ alkylthio, e.g. $C_{1-4}$ alkylthio such as methylthio or ethylthio.

As used herein, the terms "alkylamino" or "dialkylamino" are intended to include the groups —NH($R^{1a}$) and —N($R^{1a}$)($R^{1b}$) where $R^{1a}$ and $R^{1b}$ is each independently an optionally substituted straight or branched alkyl group or both together with the N atom to which they are attached form an optionally substituted heterocycloalkyl group which may contain a further heteroatom or heteroatom-containing group such as an —O— or —S— atom or a —N($R^{1a}$)— group. Particular examples of such optionally substituted heterocycloalkyl groups include optionally substituted pyrrolidinyl, piperidinyl, morpholinyl, thiomorpholinyl and N'-($C_{1-6}$ alkyl)piperazinyl groups. The optional substituents which may be present on such heterocycloalkyl groups include those optional substituents as described hereinafter in relation to aliphatic chains such as $Alk^1$.

When $Alk^1$ is present in compounds of formula (1) as an optionally substituted aliphatic chain it may be an optionally substituted $C_{1-10}$ aliphatic chain. Particular examples include optionally substituted straight or branched chain $C_{1-6}$ allylene, $C_{2-6}$ alkenylene and $C_{2-6}$ alkynylene chains.

Particular examples of aliphatic chains represented by $Alk^1$ include optionally substituted —$CH_2$—, —$CH_2CH_2$—, —$CH(CH_3)CH_2$—, —$(CH_2)_2CH_2$—, —$(CH_2)_3CH_2$—, —$CH(CH_3)(CH_2)_2CH_2$—, —$CH_2CH(CH_3)CH_2$—, —$C(CH_3)_2CH_2$—, —$CH_2C(CH_3)_2CH_2$—, —$(CH_2)_2CH(CH_3)CH_2$—, —$CH(CH_3)CH_2CH_2$—, —$CH(CH_3)CH_2CH(CH_3)CH_2$—, —$CH_2CH(CH_3)CH_2CH_2$—, —$(CH_2)_2C(CH_3)_2CH_2$—, —$(CH_2)_4CH_2$—, —$(CH_2)_5CH_2$—, —CH═CH—, —CH═$CHCH_2$—, —$CH_2CH$═CH—, —CH═$CHCH_2CH_2$—, —$CH_2CH$═$CHCH_2$—, —$(CH_2)_2CH$═CH—, —C≡C—, —C≡$CCH_2$—, —$CH_2C$≡C—, —C≡$CCH_2CH_2$—, —$CH_2C$≡$CCH_2$— and —$(CH_2)_2C$≡C— chains.

Heteroaliphatic chains represented by $Alk^1$ in the compounds of formula (1) include the aliphatic chains just described but with each additionally containing one, two, three or four heteroatoms or heteroatom-containing groups. Particular heteroatoms or groups include atoms or groups $L^2$ where $L^2$ is a linker atom or group. Each $L^2$ atom or group may interrupt the aliphatic group, or may be positioned at its terminal carbon atom to connect the group to an adjoining atom or group. Particular examples include optionally substituted -$L^2CH_2$—, —$CH_2L^2$-, -$L^2CH(CH_3)$—, —$CH(CH_3)L^2$-, —$CH_2L^2CH_2$—, -$L^2CH_2CH_2$—, -$L^2CH_2CH(CH_3)$—, —$CH(CH_3)CH_2L^2$-, —$CH_2CH_2L^2$-, —$CH_2L^2CH_2CH_2$—, —$CH_2L^2CH_2CH_2L^2$-, —$(CH_2)_2L^2CH_2$—, —$(CH_2)_3L^2CH_2$—, -$L^2(CH_2)_2CH_2$—, -$L^2CH_2CH$═CH—, —CH═$CHCH_2L^2$- and —$(CH_2)_2L^2CH_2CH_2$— chains.

When $L^2$ is present in heteroaliphatic chains as a linker atom or group it may be any divalent linking atom or group. Particular examples include —O— or —S— atoms and —C(O)—, —C(O)O—, —OC(O)—, —C(S)—, —S(O)—, —S(O)$_2$—, —N($R^3$)— (where $R^3$ is a hydrogen atom or a straight or branched alkyl group), —NR$^3$)O—, —N($R^3$)NH—, —CON($R^3$)—, —OC(O)N($R^3$)—, —CSN($R^3$)—, —N($R^3$)CO—, —N($R^3$)C(O)O—, —N($R^3$)CS—, —S(O)$_2$N($R^3$)—, —N($R^3$)S(O)$_2$—, —N($R^3$)CON($R^3$)—, —N($R^3$)CSN($R^3$)— or —N($R^3$)SO$_2$N($R^3$)— groups. Where $L^2$ contains two $R^3$ groups these may be the same or different.

The optional substituents which may be present on aliphatic or heteroaliphatic chains represented by $Alk^1$ include one, two, three or more substituents where each substituent may be the same or different and is selected from halogen atoms, e.g. fluorine, chlorine, bromine or iodine atoms, —OH, —$CO_2H$, —$CO_2R^4$ (where $R^4$ is an optionally substituted straight or branched $C_{1-6}$ alkyl group), e.g. —$CO_2CH_3$ or —$CO_2C(CH_3)_3$, —$CONHR^4$, e.g. —$CONHCH_3$, —$CON(R^4)_2$, e.g. —$CON(CH_3)_2$, —$COR^4$, e.g. —$COCH_3$, $C_{1-6}$ alkoxy, e.g. methoxy or ethoxy, halo($C_{1-6}$)alkoxy, e.g. trifluoromethoxy or difluoromethoxy, thiol (—SH), —S(O)$R^4$, e.g. —S(O)$CH_3$, —S(O)$_2R^4$, e.g. —S(O)$_2CH_3$, $C_{1-6}$ alkylthio, e.g. methylthio or ethylthio, amino, —$NHR^4$, e.g. —$NHCH_3$, and —$N(R^4)_2$, e.g. —$N(CH_3)_2$, groups. Where two $R^4$ groups are present in any of the above substituents these may be the same or different.

In addition, when two $R^4$ alkyl groups are present in any of the optional substituents just described these groups may be joined, together with the N atom to which they are attached, to form a heterocyclic ring. Such heterocyclic rings may be optionally interrupted by a further heteroatom or heteroatom-containing group selected from —O—, —S—, —N($R^4$)—, —C(O)— or —C(S)— groups. Particular examples of such heterocyclic rings include piperidinyl, pyrazolidinyl, morpholinyl, thiomorpholinyl, pyrrolidinyl, imidazolidinyl and piperazinyl rings.

When $L^1$ is present in compounds of formula (1) as a linker atom or group it may be any such atom or group as hereinbefore described in relation to $L^2$ linker atoms and groups.

Optionally substituted cycloaliphatic groups represented by the group $Cy^1$ in compounds of the invention include optionally substituted $C_{3-10}$ cycloaliphatic groups. Particular examples include optionally substituted $C_{3-10}$ cycloalkyl, e.g. $C_{3-7}$ cycloalkyl, and $C_{3-10}$ cycloalkenyl, e.g. $C_{3-7}$ cycloalkenyl, groups.

Optionally substituted heterocycloaliphatic groups represented by the group $Cy^1$ include optionally substituted $C_{3-10}$ heterocycloaliphatic groups. Particular examples include optionally substituted $C_{3-10}$ heterocycloalkyl, e.g. $C_{3-7}$ heterocycloalkyl, and $C_{3-10}$ heterocycloalkenyl, e.g. $C_{3-7}$ heterocycloalkenyl, groups, each of said groups containing one, two, three or four heteroatoms or heteroatom-containing groups $L^4$ in place of or in addition to the ring carbon atoms where $L^4$ is an atom or group as previously defined for $L^2$.

Optionally substituted polycycloaliphatic groups represented by the group $Cy^1$ include optionally substituted $C_{7-10}$ bi- or tricycloalkyl and $C_{7-10}$ bi- or tricycloalkenyl groups. Optionally substituted heteropolycycloaliphatic groups represented by the group $Cy^1$ include optionally substituted $C_{7-10}$ bi- or tricycloalkyl and $C_{7-10}$ bi- or tricycloalkenyl groups containing one, two, three, four or more $L^4$ atoms or groups in place of or in addition to the ring carbon atoms.

Particular examples of cycloaliphatic, polycycloaliphatic, heterocycloaliphatic and heteropolycycloaliphatic groups represented by the group $Cy^1$ include optionally substituted cyclopropyl, cyclobutyl, cyclopentyl, cyclohexyl, cycloheptyl, cyclobut-2-en-1-yl, cyclopent-2-en-1-yl, cyclopent-3-en-1-yl, adamantyl, norbornyl, norbornenyl, dihydrofuryl, tetrahydrofuryl, tetrahydropyranyl, dihydrothienyl, tetrahydrothienyl, pyrrolinyl, e.g. 2- or 3-pyrrolinyl, pyrrolidinyl, pyrrolidinonyl, oxazolidinyl, oxazolidinonyl, dioxolanyl, e.g. 1,3-dioxolanyl, imidazolinyl, e.g. imidazolin-2-yl, imidazolidinyl, pyrazolinyl, e.g. pyrazolin-2-yl, pyrazolidinyl, 5,6-dihydro-2(1H)-pyrazinonyl, tetrahydropyrimidinyl, thiazolinyl, thiazolidinyl, pyranyl, e.g. 2- or 4-pyranyl, piperidinyl, homopiperidinyl, heptamethyleneiminyl, piperidinonyl, 1,4-dioxanyl, morpholinyl, morpholinonyl, 1,4-dithianyl, thiomorpholinyl, piperazinyl, homopiperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5- or 1,2,6-oxathiazinyl, 1,3,5-oxadiazinyl, dihydroisothiazolyl, dihydroisothiazole 1,1-dioxide, e.g. 2,3-dihydroisothiazole 1,1-dioxide, dihydropyrazinyl and tetrahydropyrazinyl groups.

The optional substituents which may be present on the cycloaliphatic, polycycloaliphatic, heterocycloaliphatic or heteropolycycloaliphatic groups represented by the group $Cy^1$ include one, two, three or more substituents selected from halogen atoms, and $C_{1-6}$ alkyl, e.g. methyl or ethyl, halo($C_{1-6}$)alkyl, e.g. halomethyl or haloethyl such as difluoromethyl or trifluoromethyl, optionally substituted by hydroxy, e.g. —C(OH)(CF$_3$)$_2$, $C_{1-6}$ alkoxy, e.g. methoxy or ethoxy, halo($C_{1-6}$)alkoxy, e.g. halomethoxy or haloethoxy such as difluoromethoxy or trifluoromethoxy, thiol, $C_{1-6}$ alkylthio, e.g. methylthio or ethylthio, carbonyl (=O), thiocarbonyl (=S), imino (=NR$^{4a}$) (where R$^{4a}$ is an —OH group or a $C_{1-6}$ alkyl group) or -(Alk$^3$)$_v$R$^5$ groups, in which Alk$^3$ is a straight or branched $C_{1-3}$ alkylene chain, v is zero or the integer 1, and $R^5$ is a $C_{3-8}$ cycloalkyl, —OH, —SH, —N(R$^6$)(R$^7$) (in which R$^6$ and R$^7$ is each independently selected from a hydrogen atom and an optionally substituted alkyl or $C_{3-8}$ cycloalkyl group), —OR$^6$, —SR$^6$, —CN, —NO$_2$, —CO$_2$R$^6$, —SOR$^6$, —SO$_2$R$^6$, —SO$_3$R$^6$, —OCO$_2$R$^6$, —C(O)R$^6$, —OC(O)R$^6$, —C(S)R$^6$, —C(O)N(R$^6$)(R$^7$), —OC(O)N(R$^6$)(R$^7$), —N(R$^6$)C(O)R$^7$, —C(S)N(R$^6$)(R$^7$), —N(R$^6$)C(S)R$^7$, —SO$_2$N(R$^6$)(R$^7$), —N(R$^6$)SO$_2$R$^7$, —N(R$^6$)C(O)N(R$^7$)(R$^8$) (where R$^8$ is as defined for R$^6$), —N(R$^6$)C(S)N(R$^7$)(R$^8$) or —N(R$^6$)SO$_2$N(R$^7$)(R$^8$) group, or an optionally substituted aromatic or heteroaromatic group.

Particular examples of Alk$^3$ chains include —CH$_2$—, —CH$_2$CH$_2$—, —CH$_2$CH$_2$CH$_2$— and —CH(CH$_3$)CH$_2$— chains.

When $R^5$, $R^6$, $R^7$ and/or $R^8$ is present as a $C_{3-8}$ cycloalkyl group it may be, for example, a cyclopropyl, cyclobutyl, cyclopentyl or cyclohexyl group. Optional substituents which may be present on such groups include, for example, one, two or three substituents, which may be the same or different, selected from halogen atoms, for example fluorine, chlorine, bromine or iodine atoms, and hydroxy or $C_{1-6}$ alkoxy groups, e.g. methoxy, ethoxy or isopropoxy groups.

When the groups $R^6$ and $R^7$ or $R^7$ and $R^8$ are both alkyl groups these groups may be joined, together with the N atom to which they are attached, to form a heterocyclic ring. Such heterocyclic rings may be optionally interrupted by a further heteroatom or heteroatom-containing group selected from —O—, —S—, —N(R$^7$)—, —C(O)— and —C(S)— groups. Particular examples of such heterocyclic rings include piperidinyl, pyrazolidinyl, morpholinyl, thiomorpholinyl, pyrrolidinyl, imidazolidinyl and piperazinyl rings.

When $R^5$ is an optionally substituted aromatic or heteroaromatic group it may be any such group as described hereinafter in relation to $Cy^1$.

Additionally, when the group $Cy^1$ is a heterocycloaliphatic or heteropolycycloaliphatic group containing one or more nitrogen atoms each nitrogen atom may be optionally substituted by a group -(L$^5$)$_p$(Alk$^4$)$_q$R$^9$ in which $L^5$ is a —C(O)—, —C(O)O—, —C(S)—, —S(O)$_2$—, —CON(R$^6$)— or —SO$_2$N(R)— group; p is zero or the integer 1; Alk$^4$ is an optionally substituted aliphatic or heteroaliphatic chain; q is zero or the integer 1; and $R^9$ is a hydrogen atom or an optionally substituted cycloaliphatic, heterocycloaliphatic, polycycloaliphatic, heteropolycycloaliphatic, aromatic or heteroaromatic group as herein described in relation to $Cy^1$.

When Alk$^4$ is present as an aliphatic or heteroaliphatic chain it may be, for example, any aliphatic or heteroaliphatic chain as hereinbefore described for Alk$^1$.

Optionally substituted aromatic groups represented by the group $Cy^1$ include, for example, monocyclic and bicyclic fused ring $C_{6-12}$ aromatic groups, such as phenyl, 1- or 2-naphthyl, 1- or 2-tetrahydronaphthyl, indanyl or indenyl groups.

Heteroaromatic groups represented by the group $Cy^1$ include, for example, $C_{1-9}$ heteroaromatic groups containing, for example, one, two, three or four heteroatoms selected from oxygen, sulphur and nitrogen atoms. In general, the heteroaromatic groups may be, for example, monocyclic or bicyclic fused ring heteroaromatic groups. Monocyclic heteroaromatic groups include, for example, five- or six-membered heteroaromatic groups containing one, two, three or four heteroatoms selected from oxygen, sulphur and nitrogen atoms. Bicyclic heteroaromatic groups include, for example, eight- to thirteen-membered fused ring heteroaromatic groups containing one, two or more heteroatoms selected from oxygen, sulphur and nitrogen atoms.

Particular examples of heteroaromatic groups of these types include pyrrolyl, furyl, thienyl, imidazolyl, N-($C_{1-6}$ alkyl)imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,5-oxadiazolyl, 1,3,4-oxadiazolyl, 1,3,4-thiadiazolyl, pyridinyl, pyrimidinyl, pyridazinyl, pyrazinyl, 1,3,5-triazinyl, 1,2,4-triazinyl, 1,2,3-triazinyl, benzofuryl, (2,3-dihydro)benzofuryl, benzothienyl, (2,3-dihydro) benzothienyl, benzotriazolyl, indolyl, indolinyl, indazolinyl, benzimidazolyl, imidazo[1,2-a]pyridinyl, benzothiazolyl, benzoxazolyl, benzisoxazolyl, benzopyranyl, (3,4-dihydro)-benzopyranyl, quinazolinyl, quinoxalinyl, naphthyridinyl, imidazo[1,5-a]pyridinyl, imidazo[1,5-a]pyrazinyl, imidazo [1,5-c]pyrimidinyl, pyrido[3,4-b]pyridinyl, pyrido[3,2-b]pyridinyl, pyrido[4,3-b]pyridinyl, quinolinyl, isoquinolinyl, phthalazinyl, tetrazolyl, 5,6,7,8-tetrahydroquinolinyl, 5,6,7,8-tetrahydroisoquinolinyl, imidyl, e.g. succinimidyl, phthalimidyl or naphthalimidyl such as 1,8-naphthalimidyl, pyrazolo[4,3-d]pyrimidinyl, furo[3,2-d]pyrimidinyl, thieno[3,2-d]pyrimidinyl, pyrrolo[3,2-d]pyrimidinyl, pyrazolo[3,2-b] pyridinyl, furo[3,2-b]pyridinyl, thieno[3,2-b]pyridinyl, pyrrolo[3,2-b]pyridinyl, thiazolo[3,2-a]pyridinyl, pyrido[1,2-a]pyrimidinyl, tetrahydroimidazo[1,2-a]pyrimidinyl and dihydroimidazo[1,2-a]pyrimidinyl groups.

Optional substituents which may be present on aromatic or heteroaromatic groups represented by the group $Cy^1$ include one, two, three or more substituents, each selected from an atom or group $R^{10}$ in which $R^{10}$ is $R^{10a}$ or -$L^6Alk^5(R^{10a})_r$, where $R^{10a}$ is a halogen atom, or an amino (—$NH_2$), substituted amino, nitro, cyano, hydroxy (—OH), substituted hydroxy, formyl, carboxy (—$CO_2H$), esterified carboxy, thiol (—SH), substituted thiol, —$COR^{11}$ (where $R^{11}$ is an $L^6Alk^3$ $(R^{10a})_r$, aryl or heteroaryl group), —$CSR^{11}$, —$SO_3H$, —$SOR^{11}$, —$SO_2R^{11}$, —$SO_3R^{11}$, —$SO_2NH_2$, —$SO_2NHR^{11}$, —$SO_2N(R^{11})_2$, —$CONH_2$, —$CSNH_2$, —$CONHR^{11}$, —$CSNHR^{11}$, —$CON(R^{11})_2$, —$CSN(R^{11})_2$, —$N(R^{12})SO_2R^{11}$ (where $R^{12}$ is a hydrogen atom or a straight or branched alkyl group), —$N(SO_2R^{11})_2$, —$N(R^{12})SO_2NH_2$, —$N(R^{12})SO_2NHR^{11}$, —$N(R^{12})SO_2N(R^{11})_2$, —$N(R^{12})COR^{11}$, —$N(R^{12})CONH_2$, —$N(R^{12})CONHR^{11}$, —$N(R^{12})CON(R^{11})_2$, —$N(R^{12})CSNH_2$, —$N(R^{12})CSNR^{11}$, —$N(R^{12})CSN(R^{11})_2$, —$N(R^{12})CSR^{11}$, —$N(R^{12})C(O)OR^{11}$, —$SO_2NHet^1$ (where —$NHet^1$ is an optionally substituted $C_{5-7}$ cyclic amino group optionally containing one or more other —O— or —S— atoms or —$N(R^{12})$—, —C(O)— or —C(S)— groups), —$CONHet^1$, —$CSNHet^1$, —$N(R^{12})SO_2NHet^1$, —$N(R^{12})CONHet^1$, —$N(R^{12})CSNHet^1$, —$SO_2N(R^{12})Het^2$ (where -$Het^2$ is an optionally substituted monocyclic $C_{5-7}$ carbocyclic group optionally containing one or more other —O— or —S— atoms or —$N(R^{12})$—, —C(O)—, —S(O)— or —$S(O)_2$— groups), -$Het^2$, —$CON(R^{12})Het^2$, —$CSN(R^{12})Het^2$, —$N(R^{12})CON(R^{12})Het^2$, —$N(R^{12})CSN(R^{12})Het^2$, —$N(R^{12})SO_2N(R^{12})Het^2$, aryl or heteroaryl group; $L^6$ is a covalent bond or a linker atom or group as hereinbefore defined for $L^2$; $Alk^5$ is an optionally substituted straight or branched $C_{1-6}$ alkylene, $C_{2-6}$ alkenylene or $C_{2-6}$ alkynylene chain, optionally interrupted by one, two or three —O— or —S— atoms or —S(O)—, —$S(O)_2$— or —$N(R^{12})$—, e.g. —$N(CH_3)$—, groups; and r is zero or the integer 1, 2, or 3. It will be appreciated that when two $R^{11}$ or $R^{12}$ groups are present in one of the above substituents the $R^{11}$ and $R^{12}$ groups may be the same or different.

When in the group -$L^6Alk^5(R^{10a})_r$ is an integer 1, 2 or 3, it is to be understood that the substituent or substituents $R^{10a}$ may be present on any suitable carbon atom in $Alk^5$. Where more than one $R^{10a}$ substituent is present these may be the same or different and may be present on the same atom or on different atoms in $Alk^5$. Clearly, when r is zero and no substituent $R^{10a}$ is present the alkylene, alkenylene or alkynylene chain represented by $Alk^5$ becomes an alkyl, alkenyl or alkynyl group.

When $R^{10a}$ is a substituted amino group it may be, for example, a group —$NHR^{11}$ (where $R^{11}$ is as defined above) or a group —$N(R^{11})_2$ wherein each $R^{11}$ group is the same or different.

When $R^{10a}$ is a halogen atom it may be, for example, a fluorine, chlorine, bromine or iodine atom.

When $R^{10a}$ is a substituted hydroxy or substituted thiol group it may be, for example, a group —$OR^{11}$ or —$SR^{12}$ respectively.

Esterified carboxy groups represented by the group $R^{10a}$ include groups of formula —$CO_2Alk^6$ wherein $Alk^6$ is a straight or branched, optionally substituted $C_{1-8}$ alkyl group such as a methyl, ethyl, n-propyl, isopropyl, n-butyl, isobutyl, sec-butyl or tert-butyl group; a $C_{6-12}$ aryl($C_{1-8}$ alkyl) group such as an optionally substituted benzyl, phenylethyl, phenylpropyl, 1-naphthylmethyl or 2-naphthylmethyl group; a $C_{6-12}$ aryl group such as an optionally substituted phenyl, 1-naphthyl or 2-naphthyl group; a $C_{6-12}$ aryloxy($C_{1-8}$ alkyl) group such as an optionally substituted phenoxymethyl, phenoxyethyl, 1-naphthyloxymethyl or 2-naphthyloxymethyl group; an optionally substituted $C_{1-8}$ alkanoyloxy($C_{1-8}$ alkyl) group, such as a pivaloyloxymethyl, propionyloxyethyl or propionyloxypropyl group; or a $C_{6-12}$ aroyloxy($C_{1-8}$ alkyl) group such as an optionally substituted benzoyloxyethyl or benzoyloxypropyl group. Optional substituents present on the $Alk^6$ group include $R^{10a}$ atoms and groups as described above.

When $Alk^5$ is present in or as a substituent it may be, for example, a —$CH_2$—, —$CH(CH_3)$—, —$C(CH_3)$—, —$CH_2CH_2$—, —$CH_2CH_2CH_2$—, —$CH(CH_3)CH_2$—, —$CH_2CH_2CH_2CH_2$—, —$CH_2CH(CH_3)CH_2$—, —$CH(CH_3)CH_2CH_2$—, —CH=CH—, —$C(CH_3)CH_2$—, —CH=CH—, —CH=$CHCH_2$—, —$CH_2CH$=CH—, —CH=$CHCH_2CH_2$—, —$CH_2CH$=$CHCH_2$—, —$CH_2CH_2CH$=CH—, —C≡C—, —C≡$CCH_2$—, —$CH_2C$≡C—, —C≡$CCH_2CH_2$—, —$CH_2C$≡$CH_2$— or —$CH_2CH_2C$≡C— chain, optionally interrupted by one, two or three —O— or —S— atoms or —S(O)—, —$S(O)_2$— or —$N(R^{12})$—, e.g. —$N(CH_3)$—, groups. The aliphatic chains represented by $Alk^5$ may be optionally substituted by one, two or three halogen atoms in addition to any $R^{10a}$ groups that may be present.

Aryl or heteroaryl groups represented by the groups $R^{10a}$ or $R^{11}$ include mono- and bicyclic optionally substituted $C_{6-12}$ aromatic or $C_{1-9}$ heteroaromatic groups as described above for the group $Cy^1$. The aromatic and heteroaromatic groups may be attached to the group $Cy^1$ in compounds of formula (1) by any carbon atom or heteroatom, e.g. nitrogen atom, as appropriate.

It will be appreciated that when —$NHet^1$ or -$Het^2$ forms part of a substituent $R^{10}$ the heteroatoms or heteroatom-containing groups that may be present within the ring —$NHet^1$ or -$Het^2$ take the place of carbon atoms within the parent carbocyclic ring.

Thus, when —$NHet^1$ or -$Het^2$ forms part of a substituent $R^{10}$ each may be, for example, an optionally substituted pyrrolidinyl, imidazolidinyl, pyrazolidinyl, piperazinyl, morpholinyl, thiomorpholinyl, piperidinyl or thiazolidinyl group. Additionally, -$Het^2$ may represent, for example, an optionally substituted cyclopentyl or cyclohexyl group. Optional substituents which may be present on —$NHet^1$ include those substituents described above when $Cy^1$ is a heterocycloaliphatic group.

Particularly useful atoms or groups represented by $R^{10}$ include fluorine, chlorine, bromine or iodine atoms, and $C_{1-6}$ alkyl, e.g. methyl, ethyl, n-propyl, isopropyl, n-butyl or tert-butyl, optionally substituted phenyl, pyridinyl, pyrimidinyl, pyrrolyl, furyl, thiazolyl or thienyl, $C_{1-6}$ hydroxyalkyl, e.g. hydroxymethyl or hydroxyethyl, carboxy-($C_{1-6}$ alkyl), e.g. carboxyethyl, $C_{1-6}$ alkylthio, e.g. methylthio or ethylthio, carboxy($C_{1-6}$ alkyl)thio, e.g. carboxymethylthio, 2-carboxyethylthio or 3-carboxypropylthio, $C_{1-6}$ alkoxy, e.g. methoxy or ethoxy, hydroxy($C_{1-6}$ alkoxy), e.g. 2-hydroxyethoxy, optionally substituted phenoxy, pyridinyloxy, thiazolyloxy, phenylthio or pyridinylthio, $C_{3-7}$ cycloalkyl, e.g. cyclobutyl or cyclopentyl, $C_{5-7}$ cycloalkoxy, e.g. cyclopentyloxy, halo($C_{1-6}$ alkyl), e.g. trifluoromethyl, halo($C_{1-6}$ alkoxy), e.g. trifluoromethoxy, $C_{1-6}$ alkylamino, e.g. methylamino, ethylamino, —CH(CH$_3$)NH$_2$ or —C(CH$_3$)$_2$NH$_2$, halo($C_{1-6}$ alkyl)amino, e.g. fluoro($C_{1-6}$ alkyl)amino such as —CH(CF$_3$)NH$_2$ or —C(CF$_3$)$_2$NH$_2$, amino (—NH$_2$), amino($C_{1-6}$ alkyl), e.g. aminomethyl or aminoethyl, di($C_{1-6}$ alkyl)amino, e.g. dimethylamino or diethylamino, $C_{1-6}$ alkylamino($C_{1-6}$ alkyl), e.g. ethylaminoethyl, di-($C_{1-6}$ alkyl)amino($C_{1-6}$ alkyl), e.g. diethylaminoethyl, amino($C_{1-6}$ alkoxy), e.g. aminoethoxy, $C_{1-6}$ alkylamino($C_{1-6}$ alkoxy), e.g. methylaminoethoxy, di($C_{1-6}$ alkyl)amino($C_{1-6}$ alkoxy), e.g. dimethylaminoethoxy, diethylaminoethoxy, diisopropylaminoethoxy or dimethylaminopropoxy, imido, such as phthalimido or naphthalimido, e.g. 1,8-naphthalimido, nitro, cyano, hydroxy (—OH), formyl [HC(O)—], carboxy (—CO$_2$H), —CO$_2$Alk$^6$ (where Alk$^6$ is as defined above), $C_{1-6}$ alkanoyl, e.g. acetyl, optionally substituted benzoyl, thiol (—SH), thio($C_{1-6}$ alkyl), e.g. thiomethyl or thioethyl, sulphonyl (—SO$_3$H), $C_{1-6}$ alkylsulphonyl, e.g. methylsulphonyl, aminosulphonyl (—SO$_2$NH$_2$), $C_{1-6}$ alkylaminosulphonyl, e.g. methylaminosulphonyl or ethylaminosulphonyl, di($C_{1-6}$ alkyl)aminosulphonyl, e.g. dimethylaminosulphonyl or diethylaminosulphonyl, phenylaminosulphonyl, carboxamido (—CONH$_2$), $C_{1-6}$ alkylaminocarbonyl, e.g. methylaminocarbonyl or ethylaminocarbonyl, di($C_{1-6}$ alkyl)aminocarbonyl, e.g. dimethylaminocarbonyl or diethylaminocarbonyl, amino($C_{1-6}$ alkyl)aminocarbonyl, e.g. aminoethylaminocarbonyl, di($C_{1-6}$ alkyl)amino($C_{1-6}$ alkyl)aminocarbonyl, e.g. diethylaminoethylaminocarbonyl, aminocarbonylamino, $C_{1-6}$ alkylaminocarbonylamino, e.g. methylaminocarbonylamino or ethylaminocarbonylamino, di($C_{1-6}$ alkyl)aminocarbonylamino, e.g. dimethylaminocarbonylamino or diethylaminocarbonyl, amino, $C_{1-6}$ alkylaminocarbonyl($C_{1-6}$ alkyl) amino, e.g. methylaminocarbonylmethylamino, aminothiocarbonylamino, $C_{1-6}$ alkylaminothiocarbonylamino, e.g. methylaminothiocarbonylamino or ethylaminothiocarbonylamino, di($C_{1-6}$ alkylaminothiocarbonylamino, e.g. dimethylaminothiocarbonylamino or diethylaminothiocarbonylamino, $C_{1-6}$ alkylaminothiocarbonyl($C_{1-6}$ alkyl)amino, e.g. ethylaminothiocarbonylmethylamino, —CONHC(=NH)NH$_2$, $C_{1-6}$ alkylsulphonylamino, e.g. methylsulphonylamino or ethylsulphonylamino, di($C_{1-6}$ alkyl)sulphonylamino, e.g. dimethylsulphonylamino or diethylsulphonylamino, optionally substituted phenylsulphonylamino, aminosulphonylamino (—NHSO$_2$ NH$_2$), $C_{1-6}$ alkylaminosulphonylamino, e.g. methylaminosulphonylamino or -ethylaminosulphonylamino, di($C_{1-6}$ alkyl)aminosulphonylamino, e.g. dimethylamino-sulphonylamino or diethylaminosulphonylamino, optionally substituted morpholinylsulphonylamino or morpholinylsulphonyl($C_{1-4}$ alkyl)amino, optionally substituted phenylaminosulphonylamino, $C_{1-6}$ alkanoylamino, e.g. acetylamino, amino($C_{1-6}$ alkanoyl)amino, e.g. aminoacetylamino, di($C_{1-6}$ alkyl)amino ($C_{1-6}$ alkanoyl)-amino, e.g. dimethylaminoacetylamino, $C_{1-6}$ alkanoylamino($C_{1-6}$ alkyl), e.g. acetylamiinomethyl, $C_{1-6}$ alkanoylamino($C_{1-6}$ alkyl)amino, e.g. acetamidoethylamino, $C_{1-6}$ alkoxycarbonylamino, e.g. methoxycarbonylamino, ethoxycarbonylamino or tert-butoxycarbonylamino, or optionally substituted benzyloxy, pyridinylmethoxy, thiazolylmethoxy, benzyloxycarbonylamino, benzyloxycarbonylamino($C_{1-6}$ alkyl), e.g. benzyloxycarbonylaminoethyl, benzothio, pyridinylmethylthio or thiazolylmethylthio groups.

A further particularly useful group of substituents represented by $R^{10}$ when present on aromatic or heteroaromatic groups includes substituents of formula -L$^6$Alk$^5$R$^{10a}$ where L$^6$ is preferably a covalent bond, an —O— or —S— atom or a —N(R$^3$)—, —C(O)—, —C(O)O—, —OC(O)—, —N(R$^3$)CO—, —CON(R$^3$)— or —N(R$^3$)S(O)$_2$— group; Alk$^5$ is an optionally substituted $C_{1-6}$ alkylene group optionally interrupted by one or two —O— or —S— atoms or —N(R$^{12}$)—, —C(O)—, —C(S)—, —CON(R$^{12}$)— or —N(R$^{12}$)CO— groups; and R$^{10a}$ is an optionally substituted -Het$^2$ group as herein defined or an optionally substituted heteroaromatic group as hereinbefore described in relation to Cy$^1$.

Where desired, two $R^{10}$ substituents may be linked together to form a cyclic group such as a cyclic ether, e.g. a $C_{1-6}$ alkylenedioxy group such as methylenedioxy or ethylenedioxy.

It will be appreciated that where two or more $R^{10}$ substituents are present, these need not necessarily be the same atoms and/or groups. In general, the substituent(s) may be present at any available ring position on the aromatic or heteroaromatic group represented by the group Cy$^1$.

The optionally substituted aromatic or heteroaromatic group represented by Ar in compounds of the invention may be any aromatic or heteroaromatic group as hereinbefore described for Cy$^1$. Optional substituents which may be present include those $R^{10}$ atoms and groups as generally or particularly described in relation to Cy$^1$ aromatic and heteroaromatic groups.

In general, in compounds of formula (1) X is preferably an —O— or —S— atom, and is especially a —S— atom.

In another group of compounds of formula (1) $R^a$ is preferably a hydrogen atom or a $C_{1-4}$ alkyl group, especially a methyl, ethyl, n-propyl or isopropyl group. In particular, $R^a$ is a methyl group or more especially a hydrogen atom.

In another particular class of compounds of formula (1) the bond represented by the dashed line is present and A is a —C(R$^b$)= group. In these compounds $R^b$ is preferably a hydrogen atom or a $C_{1-4}$ alkyl group, especially a methyl, ethyl, n-propyl or isopropyl group. More particularly, $R^b$ is a methyl group or more especially a hydrogen atom.

When in compounds of formula (1) n is the integer 1, Alk$^1$ is preferably an optionally substituted $C_{1-6}$ alkylene chain, especially an optionally substituted —CH$_2$—, —CH$_2$CH$_2$—, —CH$_2$CH$_2$CH$_2$—, —CH(CH$_3$)CH$_2$— or —CH$_2$CH (CH$_3$)— chain, more especially a —CH$_2$— or —CH$_2$CH$_2$— chain, and most especially a —CH$_2$— chain.

In one class of compounds of formula (1) n is zero.

The group L$^1$ in compounds of formula (1) is preferably a covalent bond, an —O— or —S— atom or an —N(R$^3$)—, especially —NH— or —N(CH$_3$)—, —C(O)—, —C(S)—, —S(O)— or —S(O)$_2$— group. More particularly, L$^1$ is a covalent bond, an —O— or —S— atom or a —NH— group. L$^1$ is most preferably a covalent bond.

Cy$^1$ in compounds of formula (1) is preferably an optionally substituted cycloaliphatic, aromatic or heteroaromatic group as hereinbefore generally and particularly defined.

Particularly preferred Cy$^1$ optionally substituted cycloaliphatic groups include optionally substituted $C_{3-7}$ cycloalkyl groups, especially cyclopropyl, cyclobutyl, cyclopentyl or cyclohexyl groups.

Particularly preferred optional substituents which may be present on Cy$^1$ optionally substituted cycloaliphatic groups include halogen atoms, especially fluorine, chlorine or bromine atoms, $C_{1-6}$ alkyl groups, especially $C_{1-3}$ alkyl groups, most especially a methyl group, halo($C_{1-6}$ alkyl) groups, especially fluoro($C_{1-6}$ alkyl) groups, most especially a —CF$_3$ group, $C_{1-6}$ alkoxy groups, especially a methoxy, ethoxy, propoxy or isopropoxy group, and halo($C_{1-6}$ alkoxy) groups, especially fluoro($C_{1-6}$ alkoxy) groups, most especially a —OCF$_3$ group, or a cyano (—CN), esterified carboxy, especially —CO$_2$CH$_3$ or —CO$_2$C(CH$_3$)$_3$, nitro (—NO$_2$), amino (—NH$_2$), substituted amino, especially —NHCH$_3$ or —N(CH$_3$)$_2$, —C(O)R$^6$, especially —C(O)$_9$H$_3$, or —N(R$^6$)C(O)R$^7$, especially —NHCOCH$_3$, group.

Particularly preferred Cy$^1$ aromatic groups include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur and nitrogen atoms. Particularly preferred optionally substituted monocyclic heteroaromatic groups include optionally substituted furyl, thienyl, pyrrolyl, oxazolyl, thiazolyl, pyridinyl, pyrimidinyl and triazinyl groups.

Particularly preferred optional substituents which may be present on Cy$^1$ aromatic or heteroaromatic groups include atoms or groups —R$^{10a}$ and -L$^6$Alk$^5$(R$^{10a}$)$_r$ as hereinbefore defined. Particularly useful optional substituents include halogen atoms, especially fluorine, chlorine or bromine atoms, C$_{1-6}$ alkyl groups, especially C$_{1-3}$ alkyl groups, most especially a methyl group, halo(C$_{1-6}$ alkyl) groups, especially fluoro(C$_{1-6}$ alkyl) groups, most especially a —CF$_3$ group, C$_{1-6}$ alkoxy groups, especially a methoxy, ethoxy, n-propoxy or isopropoxy group, and halo(C$_{1-6}$ alkoxy) groups, especially fluoro(C$_{1-6}$ alkoxy) groups, most especially a —OCF$_3$ group, or a cyano (—CN), carboxy (—CO$_2$H), esterified carboxy (—CO$_2$Alk$^6$), especially —CO$_2$CH$_3$, —CO$_2$CH$_2$CH$_3$ or —CO$_2$C(CH$_3$)$_3$, nitro (—NO$_2$), amino (—NH$_2$), substituted amino, especially —NHCH$_3$ or —N(CH$_3$)$_2$, —COR$^{11}$, especially —COCH$_3$, or —N(R$^{12}$)COR$^{11}$, especially —NHCOCH$_3$, group.

Further preferred optional substituents which may be present on Cy$^1$ aromatic or heteroaromatic groups include groups of formula -L$^6$Alk$^5$(R$^{10a}$)$_r$ in which r is the integer 1; L$^6$ is a covalent bond, an —O— or —S— atom, or a —N(R$^3$)—, especially —NH— or —N(CH$_3$)—, —C(O)—, —C(S)—, —C(O)O—, —OC(O)—, —N(R$^3$)CO—, especially —NHCO—, or —CON(R$^3$)—, especially —CONH—, group; Alk$^5$ is a C$_{1-6}$ alkylene chain, especially a —CH$_2$—, —CH$_2$CH$_2$—, —CH$_2$CH$_2$CH$_2$— or —CH$_2$CH$_2$CH$_2$CH$_2$— chain; and R$^{10a}$ is a substituted hydroxy group, especially a —OCH$_3$, —OCH$_2$CH$_3$ or —OCH(CH$_3$)$_2$ group, a substituted amino group, especially a —N(CH$_3$)$_2$ or —N(CH$_2$CH$_3$)$_2$ group, or a -Het$^2$ group, especially an optionally substituted monocyclic C$_{5-7}$ carbocyclic group containing one, two or three —O—, —S—, —N(R$^{12}$)—, especially —NH— or —N(CH$_3$)—, or —C(O)— groups within the ring structure as previously described, most especially an optionally substituted pyrrolidinyl, imidazolidinyl, piperidinyl, e.g. N-methylpiperidinyl, morpholinyl, thiomorpholinyl or piperazinyl group, or R$^{10a}$ is an optionally substituted heteroaromatic group, especially a five- or six-membered monocyclic heteroaromatic group containing one, two, three or four heteroatoms selected from oxygen, sulphur and nitrogen atoms, such as an optionally substituted pyrrolyl, furyl, thienyl, imidazolyl, triazolyl, pyridinyl, pyrimidinyl, triazinyl, pyridazinyl or pyrazinyl group. Particularly preferred optional substituents on the -Het$^2$ groups just described include hydroxy (—OH) and carboxy (—CO$_2$H) groups or those preferred optional substituents just described in relation to the group Cy$^1$.

In one particularly preferred group of compounds of formula (1) Cy$^1$ is an optionally substituted phenyl group, especially a phenyl group optionally substituted by one, two or three optional substituents where at least one, and preferably two, optional substituents are located ortho to the bond joining Cy$^1$ to the remainder of the compound of formula (1). Particularly preferred ortho substituents include halogen atoms, especially fluorine or chlorine atoms, C$_{1-3}$ alkyl groups, especially methyl, C$_{1-3}$ alkoxy groups, especially methoxy, halo(C$_{1-3}$ alkyl) groups, especially —CF$_3$, halo (C$_{1-3}$ alkoxy) groups, especially —OCF$_3$, and cyano (—CN) groups. In this class of compounds a second or third optional substituent when present in a position other than the ortho positions of the ring Cy$^1$ may be preferably an atom or group —R$^{10a}$ or -L$^6$Alk$^5$(R$^{10a}$)$_r$ as herein generally and particularly described.

In one specific embodiment, Cy$^1$ is phenyl. In another specific embodiment, Cy$^1$ is cyclopropyl.

The group Y in compounds of formula (1) is preferably a —CH= group or a substituted carbon atom. Particular substituted carbon atoms include those where Y is —C(R$^{10}$)= wherein R$^{10}$ is as generally or particularly described above, especially those —R$^{10a}$ and -L$^6$Alk$^5$(R$^{10a}$)$_r$ substituents just described with respect to those preferred optional substituents present on Cy$^1$ aromatic or heteroaromatic groups. Particularly useful compounds of formula (1) are those compounds wherein Y is —CH= or —C(R$^{10}$)= in which R$^{10}$ is a —CN, —CONH$_2$, —CONHR$^{11}$, —CON(R$^{11}$)$_2$, —CONHet$^1$, —CON(R$^{12}$)Het$^2$, —CON(R$^{12}$)Alk$^5$Het$^2$, or esterified carboxy, particularly —CO$_2$Alk$^6$, group as generally or particularly described herein. Especially favoured compounds of formula (1) are those compounds wherein Y is —C(R$^{10}$)= in which R$^{10}$ is —CN, —CONH$_2$ or —CO$_2$Alk$^6$ and Alk$^6$ is C$_{1-4}$ alkyl (especially ethyl).

LAr in compounds of the invention may typically be —OAr, —SAr, —C(R$^{3a}$)(R$^{3b}$)Ar [especially —CH$_2$Ar or —CH(OH)Ar], —C(R$^{3a}$)(R$^{3b}$)CH$_2$Ar (especially —CH$_2$CH$_2$Ar), —N(R$^{3c}$)NHAr (especially —NHNHAr), —N(R$^{3c}$)CH$_2$Ar [especially —NHCH$_2$Ar or —N(CH$_3$)CH$_2$Ar], —N(R$^{3c}$)C(R$^{3a}$)R$^{3b}$)Ar [especially —NHCH(CH$_3$)Ar], —N(R$^{3c}$)COAr (especially —NHCOAr), —S(O)$_2$N(R$^{3c}$)Ar (especially —SO$_2$NHAr), —N(R$^{3c}$)S(O)$_2$Ar (especially —NHSO$_2$Ar) or —N(R$^{3c}$)CON(R$^{3d}$d)Ar (especially —NHCONHAr).

LAr in compounds of the invention may in particular be an —OAr, —SAr, —C(R$^{3a}$)(R$^{3b}$)Ar, especially —CH$_2$Ar, or —N(R$^{3c}$)CH$_2$Ar, especially —NHCH$_2$Ar, group.

Particularly preferred Ar aromatic groups in compounds of formula (1) include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur and nitrogen atoms. Particularly preferred optionally substituted monocyclic heteroaromatic groups include optionally substituted furyl, thienyl, pyrrolyl, oxazolyl, thiazolyl, pyridinyl, pyrimidinyl or triazinyl groups.

Particularly preferred optional substituents which may be present on Ar aromatic or heteroaromatic groups include atoms or groups —R$^{10a}$ or -L$^6$Alk$^5$(R$^{10a}$)$_r$ as hereinbefore defined. Particularly useful optional substituents include halogen atoms, especially fluorine, chlorine or bromine atoms, C$_{1-6}$ alkyl groups, especially C$_{1-3}$ alkyl groups, most especially a methyl group, halo(C$_{1-6}$ alkyl) groups, especially fluoro(C$_{1-6}$ alkyl) groups, most especially a —CF$_3$ group, C$_{1-6}$ alkoxy groups, especially a methoxy, ethoxy, n-propoxy or isopropoxy group, and halo(C$_{1-6}$ alkoxy) groups, especially fluoro(C$_{1-6}$ alkoxy) groups, most especially a —OCF$_3$ group, or a cyano (—CN), esterified carboxy, especially —CO$_2$CH$_3$ or —CO$_2$C(CH$_3$)$_3$, nitro (—NO$_2$), amino (—NH$_2$), substituted amino, especially —NHCH$_3$ or —N(CH$_3$)$_2$, —COR$^{11}$, especially —COCH$_3$, or —N(R$^{12}$)COR$^{11}$, especially —NHCOCH$_3$, group.

Particularly useful Ar groups in compounds of formula (1) include phenyl and mono- or disubstituted phenyl groups in which each substituent is in particular a —R$^{10a}$ or -L$^6$Alk$^5$(R$^{10a}$)$_r$ atom or group as just defined and is especially a halogen atom or a C$_{1-3}$ alkyl, C$_{1-3}$ alkoxy or —CN group.

Specific Ar groups in the compounds of formula (1) above include phenyl, halophenyl (especially chlorophenyl; in particular 4-chlorophenyl), dihalophenyl (especially difluorophenyl; in particular 2,6-difluorophenyl), (C$_{1-6}$ alkyl)phenyl (especially methylphenyl; in particular 3-methylphenyl or 4-methylphenyl), pyridinyl (in particular pyridin-2-yl) and (C$_{1-6}$ alkyl)pyridinyl (especially methylpyridinyl; in particular 6-methylpyridin-2-yl).

Particularly useful compounds of the invention include each of the compounds described in the Examples hereinafter, and the salts, solvates, hydrates and N-oxides thereof.

Compounds according to the invention are potent and selective inhibitors of p38 kinases, including all isoforms and splice variants thereof. More specifically, the compounds of the invention are inhibitors of p38α, p38β and p38β2. The ability of the compounds to act in this way may be simply determined by employing tests such as those described in the Examples hereinafter.

The compounds of formula (1) are of use in modulating the activity of p38 kinases and in particular are of use in the prophylaxis and treatment of any p38 kinase mediated diseases or disorders in a human or other mammal. The invention extends to such a use and to the use of the compounds for the manufacture of a medicament for treating such diseases or disorders. Furthermore, the invention extends to the administration to a human of an effective amount of a p38 inhibitor for treating any such disease or disorder.

The invention also extends to the prophylaxis or treatment of any disease or disorder in which p38 kinase plays a role including conditions caused by excessive or unregulated pro-inflammatory cytokine production, including for example excessive or unregulated TNF, IL-1, IL-6 and IL-8 production in a human or other mammal. The invention extends to such a use and to the use of the compounds for the manufacture of a medicament for treating such cytokine-mediated diseases or disorders. Furthermore, the invention extends to the administration to a human of an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation and conditions associated with prostaglandin endoperoxidase synthetase-2 (COX-2).

Autoimmune diseases which may be prevented or treated include but are not limited to rheumatoid arthritis, inflammatory bowel disease, ulcerative colitis, Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs host disease and psoriasis.

The invention further extends to the particular autoimmune disease rheumatoid arthritis.

Inflammatory diseases which may be prevented or treated include but are not limited to asthma, allergies, respiratory distress syndrome, and acute or chronic pancreatitis.

Destructive bone disorders which may be prevented or treated include but are not limited to osteoporosis, osteoarthritis and multiple myeloma-related bone disorder.

Proliferative diseases which may be prevented or treated include but are not limited to acute or chronic myelogenous leukemia, Kaposi's sarcoma, metastatic melanoma and multiple myeloma.

Neurodegenerative diseases which may be prevented or treated include but are not limited to Parkinson's disease, Alzheimer's disease, cerebral ischemias and neurodegenerative disease caused by traumatic injury.

Viral diseases which may be prevented or treated include but are not limited to acute hepatitis infection (including hepatitis A, hepatitis B and hepatitis C), HIV infection and CMV retinitis.

Infectious diseases which may be prevented or treated include but are not limited to septic shock, sepsis and Shigellosis.

In addition, p38 inhibitors of this invention exhibit inhibition of expression of inducible pro-inflammatory proteins such as prostaglandin endoperoxidase synthetase-2, otherwise known as cyclooxygenase-2 (COX-2), and are therefore of use in therapy. Pro-inflammatory mediators of the cyclooxygenase pathway derived from arachidonic acid are produced by inducible COX-2 enzyme. Regulation of COX-2 would regulate these pro-inflammatory mediators such as prostaglandins, which affect a wide variety of cells and are important and critical inflammatory mediators of a wide variety of disease states and conditions. In particular, these inflammatory mediators have been implicated in pain, such as in the sensitization of pain receptors, or edema. Accordingly, additional p38-mediated conditions which may be prevented or treated include edema, analgesia, fever and pain such as neuromuscular pain, headache, dental pain, arthritis pain and pain caused by cancer.

As a result of their p38 inhibitory activity, compounds of the invention have utility in the prevention and treatment of diseases associated with cytokine production including but not limited to those diseases associated with TNF, IL-1, IL-6 and IL-8 production.

TNF-mediated diseases or conditions include for example rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoidosis, bone resportion disease, reperfusion injury, graft vs host reaction, allograft rejections, fever and myalgias due to infection, cachexia secondary to infection, AIDS, ARC or malignancy, keloid formation, scar tissue formation, Crohn's disease, ulcerative colitis, pyresis, and viral infections such as HIV, CMV, influenza and herpes; veterinary viral infections such as lentivirus infections, including but not limited to equine infectious anemia virus, caprine arthritis virus, visna virus or maedi virus; and retrovirus infections, including feline immunodeficiency virus, bovine immunodeficiency virus and canine immunodeficiency virus.

Compounds of the invention may also be used in the treatment of viral infections, where such viruses elicit TNF production in vivo or are sensitive to upregulation by TNF. Such viruses include those that produce TNF as a result of infection and those that are sensitive to inhibition, for instance as a result of decreased replication, directly or indirectly by the TNF-inhibiting compounds of the invention. Such viruses include, but are not limited to, HIV-1, HIV-2 and HIV-3, Cytomegalovirus (CMV), influenza, adenovirus and the herpes group of viruses such as Herpes zoster and Herpes simplex.

IL-1 mediated diseases or conditions include for example rheumatoid arthritis, osteoarthritis, psoriatic arthritis, traumatic arthritis, rubella arthritis, inflammatory bowel disease, stroke, endotoxemia and/or toxic shock syndrome, inflammatory reaction induced by endotoxin, diabetes, pancreatic β-cell disease, Alzheimer's disease, tuberculosis, atherosclerosis, muscle degeneration and cachexia.

IL-8 mediated diseases and conditions include for example those characterized by massive neutrophil infiltration such as psoriasis, inflammatory bowel disease, asthma, cardiac, brain and renal reperfusion injury, adult respiratory distress syndrome, thrombosis and glomerulonephritis. The increased IL-8 production associated with each of these diseases is responsible for the chemotaxis of neutrophils into inflammatory sites. This is due to the unique property of IL-8 (in comparison to TNF, IL-1 and IL-6) of promoting neutrophil chemotaxis and activation. Therefore, inhibition of IL-8 production would lead to a direct reduction in neutrophil infiltration.

It is also known that both IL-6 and IL-8 are produced during rhinoviras (HRV) infections and contribute to the pathogenesis of the common cold and exacerbation of asthma associated with HRV infection [Turner et al., *Clin. Infec. Dis.*, 1997, 26, 840; Grunberg et al., *Am. J. Crit. Care Med.*, 1997, 155, 1362; Zhu et al., *J. Clin. Invest.*, 1996, 97, 421]. It has also been demonstrated in vitro that infection of pulmonary epithelial cells (which represent the primary site of infection by HRV) with HRV results in production of IL-6 and IL-8 [Sabauste et al., *J. Clin. Invest.*, 1995, 96, 549]. Therefore, p38 inhibitors of the invention may be used for the treatment or prophylaxis of the common cold or respiratory viral infection caused by human rhinoviras infection (HRV), other enteroviruses, coronavirus, influenza virus, parainfluenza virus, respiratory syncytial virus or adenovirus.

For the prophylaxis or treatment of a p38 or pro-inflammatory cytokine mediated disease the compounds according to the invention may be administered to a human or mammal as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (1) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of the invention may be prepared by a number of processes as generally described below and more specifically in the Examples hereinafter. In the following process description, the symbols Ar, $Cy^1$, $Alk^1$, n, $L^1$, L, $R^a$, $R^b$, $R^c$, A, X and Y when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Greene, T. W. and Wuts, P. G. M., *Protective Groups in Organic Synthesis*, John Wiley and Sons, $3^{rd}$ edition, 1999]. In some instances, deprotection may be the final step in the synthesis of a compound of formula (1) and the processes according to the invention described hereinafter are to be understood to extend to such removal of protecting groups.

Thus, according to a further aspect of the invention a compound of formula (1) in which A is a —$C(R^b)$= group, X is an —O— or —S— atom or a —NH— group, Y is a substituted carbon atom in which the substituent is an esterified carboxy group, for example a —$CO_2Alk^6$ group, and L is a —$NHCH_2$— chain may be prepared according to the reactions set out in Scheme 1 below. In the Scheme the preparation of an ethyl ester is specifically shown, but it will be appreciated that other esters may be obtained by simply varying the ester starting material and if appropriate any reaction conditions:

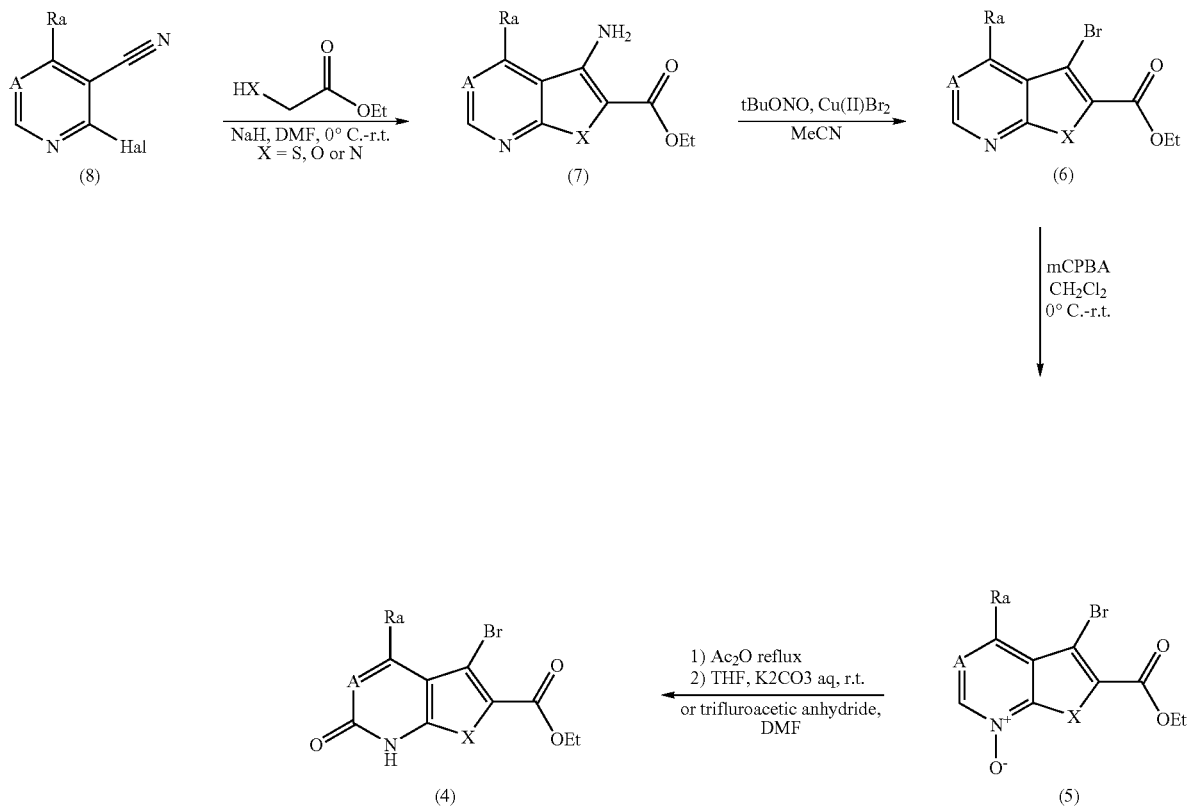

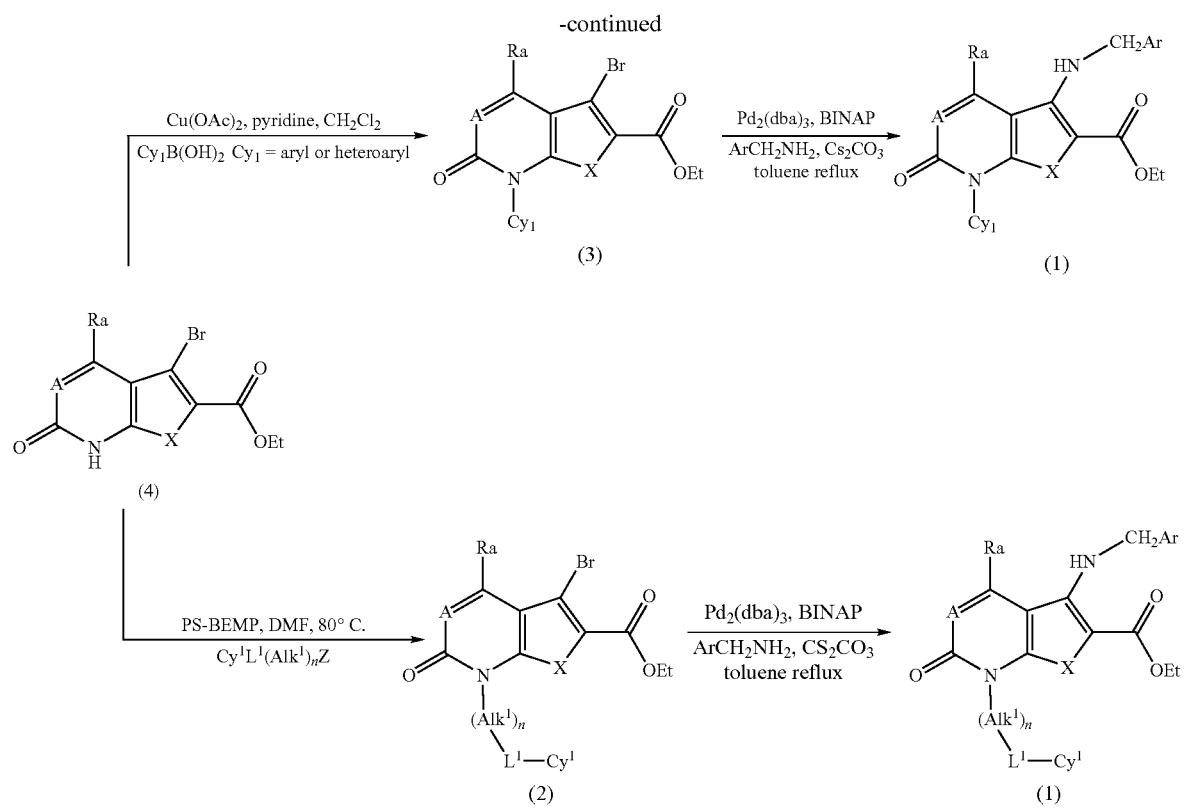

Thus, in Scheme 1 a compound of formula (1) may be prepared by reaction of a compound of formula (2) or (3) with an amine ArCH$_2$NH$_2$ in the presence of a palladium catalyst. The reaction may be conveniently carried out in a solvent such as toluene at an elevated temperature, e.g. the reflux temperature, using a catalyst such as tris(dibenzylideneacetone)dipalladium(0), a phosphine ligand such as 2,2'-bis(diphenylphosphino)-1,1'-binaphthyl and a base such as caesium carbonate. Where desired, alternative reaction conditions may be used, for example as described in the literature [Luker et al., *Tetrahedron Lett.*, 2001, 41, 7731; Buchwald, S. L., *J. Org. Chem.*, 2000, 65, 1144; Hartwig, J. F., *Angew. Chem. Int. Ed. Engl.*, 1998, 37, 2046].

Intermediates of formula (2) may be prepared by reaction of a compound of formula (4) with an alkylating agent of formula Cy$^1$L$^1$(Alk$^1$)$_n$Z, where Z is a leaving group such as a halogen atom, e.g. a chlorine, bromine or iodine atom, or a sulphonyloxy group such as an alkylsulphonyloxy, e.g. trifluoromethylsulphonyloxy, or arylsulphonyloxy, e.g. phenylsulphonyloxy, group.

The reaction may be performed in the presence of a solvent, for example a substituted amide such as N,N-dimethylformamide, optionally in the presence of a base, for example an inorganic base such as sodium hydride, or an organic base such as an organic amine, e.g. a cyclic amine such as 1,5-diazabicyclo[4.3.0]non-5-ene, or a resin-bound organic amine such as resin-bound 2-tert-butylimino-2-diethylamino-1,3-dimethylperhydro-1,3,2-diazaphosphorine (PS-BEMP), at an elevated temperature, for example 60 to 100° C.

Intermediates of formula (3) may be prepared by the reaction of a compound of formula (4) with a boronic acid of formula Cy$^1$B(OH)$_2$ in which Cy$^1$ is an aryl or heteroaryl group. The reaction may be performed in an organic solvent, for example a halogenated hydrocarbon such as dichloromethane or dichloroethane, in the presence of a copper reagent, for example a copper(II) reagent such as copper(II) acetate, optionally in the presence of an oxidant, for example 2,2,6,6-tetramethyl-1-piperidinyloxy or pyridine N-oxide, optionally in the presence of a base, for example an organic amine such as an alkylamine, e.g. triethylamine, or an aromatic amine, e.g. pyridine, at a temperature from around ambient to the reflux temperature [see, for example, Chan, D. T. et al., *Tetrahedron Lett.*, 1998, 2933; Lam, P. Y. S. et al., *Tetrahedron Lett.*, 2001, 3415].

It will be appreciated that if desired the reactions just described may be carried out in the reverse order so that the amination using ArCH$_2$NH$_2$ is performed first with the intermediate of formula (4) followed by alkylation/arylation to yield the compound of formula (1).

Intermediate pyridinones of formula (4) may be prepared from pyridine N-oxides of formula (5) by sequential reaction with an anhydride, for example acetic anhydride, at an elevated temperature, for example the reflux temperature, followed by reaction with an inorganic base, for example a carbonate such as aqueous potassium carbonate, in a solvent such as an ether, for example a cyclic ether, e.g. tetrahydrofuran, at around ambient temperature. Alternatively, the reaction may be performed using trifluoroacetic anhydride in N,N-dimethylformamide from 0° C. to ambient temperature conditions [see, for example, Konno et al., *Heterocycles*, 1986, 24, 2169].

Pyridine N-oxides of formula (5) may be formed by oxidation of pyridines of formula (6) using an oxidising agent such as hydrogen peroxide in the presence of an acid such as acetic acid, at an elevated temperature, for example around 70° C. to 80° C.; or alternatively by reaction with a peracid such as peracetic acid or m-chloroperoxybenzoic acid in a solvent such as a halogenated hydrocarbon, e.g. dichloromethane, or an alcohol, e.g. tert-butanol, at a temperature from the ambient temperature to the reflux temperature.

Intermediate pyridines of formula (6) in Scheme 1 may be obtained by standard methods such as, for example, the Sandmeyer reaction. Thus, for example, a bromide of formula (6) may be prepared by treatment of an aryl amine of formula (7) with an alkyl nitrite, for example tert-butyl nitrite, and a copper salt, for example copper(II) bromide, in the presence of a solvent, for example a nitrile such as acetonitrile, at a temperature from about 0° C. to around 65° C.

Amines of formula (7) may be formed from 2-halopyridine-3-carbonitriles of formula (8) by reaction with a reagent of formula $HXCH_2CO_2Et$ (where Et is an ethyl group and X is an —O— or —S— atom or a —NH— group). The reaction may be performed in the presence of a solvent such as a substituted amide, for example N,N-dimethylformamide, an ether, e.g. a cyclic ether such as tetrahydrofuran, or an alcohol such as ethanol, in the presence of a base, for example an inorganic base such as sodium carbonate, a hydride, e.g. sodium hydride, or an organic base such as 1,5-diazabicyclo[4.3.0]non-5-ene or a trialkylamine such as triethylamine, at a temperature between about 0° C. and 100° C. The carbonitrile starting materials are readily available or may be obtained from known compounds using standard procedures.

The intermediate pyridinones of formula (4) are useful for obtaining other compounds of the invention using standard coupling or displacement reactions.

Thus, for example, palladium-catalysed coupling such as described for the amination above additionally may be generally employed with a pyridinone of formula (2) or (3) [obtainable from compound (4)] and any other amine, amide, urea and other appropriate starting materials $Ar(CH_2)_q HetH$ (including, for example, a starting material of formula $ArNHNH_2$) to obtain a compound of the invention.

In another example, compounds of formula (15 in which the ArL- group is linked to the remainder of the compound through a carbon atom may be obtained by palladium coupling using a reagent such as tetrakis(triphenylphosphine)palladium(0), an intermediate of formula (2) or (3) [obtainable from compound (4)], a halide $Ar(CH_2)_q HetCH_2Hal$ (where Hal is a halogen atom such as a bromine atom) or $Ar(CH_2)_q CR^{3a}R^{3b}Hal$, and activated zinc, in a solvent such as tetrahydrofuran at an elevated temperature.

In a further example, compounds of formula (1) in which L is a —$S(CH_2)_q$— atom or chain may be obtained by displacement of the bromine atom in a pyridinone of formula (2) or (3) [obtainable from compound (4)] using a thiol $Ar(CH_2)_q SH$ and a base such as potassium carbonate or sodium hydride in a solvent such as N,N-dimethylformamide, if necessary at an elevated temperature. Similarly, the bromine atom in a pyridinone of formula (2) or (3) [obtainable from compound (4)] may be displaced using a compound $Ar(CH_2)_q OH$ in the presence of Cu(II)O, a base such as potassium carbonate and a solvent such as pyridine at an elevated temperature, to yield a compound of the invention in which L is a —$O(CH_2)_q$— atom or chain.

In a still further example, compounds of formula (1) in which L is a —$CH(OH)(CH_2)_q$— chain may be obtained by reacting compound (2) or (3) with a base such as n-butyllithium or tert-butyllithium in a suitable solvent, e.g. tetrahydrofuran, followed by treatment with an aldehyde $Ar(CH_2)_q CHO$.

In a yet further example, compounds of formula (1) in which L is a —$S(O)_2NH(CH_2)_q$— chain may be obtained by reacting compound (2) or (3) with a base such as n-butyllithium in a suitable solvent, e.g. tetrahydrofuran, then with sulphur dioxide, followed by treatment with a halogenating agent such as N-chloro-succinimide, and subsequently with a reagent of formula $Ar(CH_2)_q NH_2$, typically in the presence of pyridine and 4-(dimethylamino)pyridine.

Compounds of formula (1) in which L is a —$CH_2CH_2$— chain may be obtained from a precursor compound, corresponding to a compound of formula (1) as depicted above in which L represents —C≡C—, by reduction, for example by catalytic hydrogenation whereby the requisite precursor compound is treated with hydrogen in the presence of a hydrogenation catalyst, e.g. palladium on charcoal, in a solvent such as ethanol. The precursor compound may in turn be obtained by reacting a compound of formula (2) or (3) with a compound of formula Ar—C≡CH in the presence of a transition metal catalyst, e.g. dichlorobis(triphenylphosphine)-palladium(II), which reaction may conveniently be effected at an elevated temperature in a solvent such as 1,2-dimethoxyethane, typically in the presence of copper(I) iodide and an organic base such as diisopropylethylamine.

Conditions analogous to those described above for converting a compound of formula (2) or (3) as depicted above into a compound of formula (1) may also be employed for converting a compound of formula (2) or (3) wherein the ethyl ester moiety is replaced by another suitable substituent, e.g. cyano (—CN) or carboxamido (—$CONH_2$), into the corresponding compound of formula (1) wherein Y is a substituted carbon atom in which the substituent is other than an ethyl ester moiety (e.g. compounds wherein this moiety is —CN or —$CONH_2$). The relevant precursors of formula (2) or (3) wherein the ethyl ester moiety is replaced by another suitable substituent, e.g. cyano (—CN) or carboxamido (—$CONH_2$), may be prepared by the rocedures described in the accompanying Examples, or by methods analogous hereto.

Compounds of formula (1) in which L is a —$NHCO(CH_2)_q$— chain may be obtained from a precursor compound, corresponding to a compound of formula (1) as depicted above in which -LAr represents —$NH_2$, by reaction with an acylating agent of formula $Ar(CH_2)_q C(O)Hal$ (wherein Hal represents a halogen atom, e.g. chloro), which reaction is conveniently effected in the presence of an organic base such as triethylamine, 4-(dimethylamino)pyridine, and a solvent such as dichloromethane.

Compounds of formula (1) in which L is a —$NHSO_2(CH_2)_q$— chain may be obtained from a precursor compound, corresponding to a compound of formula (1) as depicted above in which -LAr represents —$NH_2$, by reaction with a compound of formula $Ar(CH_2)_q S(O)_2 Hal$ (wherein Hal represents a halogen atom, e.g. chloro), which reaction is conveniently effected in the presence of a strong base such as sodium hydride, in a solvent such as N,N-dimethylformamide.

Compounds of formula (1) in which L is a —$NHCONH(CH_2)_q$— chain may be obtained from a precursor compound, corresponding to a compound of formula (1) as depicted above in which -LAr represents —$NH_2$, by reaction with phosgene in a suitable solvent, e.g. a mixture of toluene and dichloromethane, typically at a temperature in the region of 0° C., followed by reaction with an amine of formula $Ar(CH_2)_q NH_2$, which reaction is conveniently effected in the presence of an organic base such as triethylamine.

The precursor compound referred to immediately above, corresponding to a compound of formula (1) as depicted above in which -LAr represents —$NH_2$, may be obtained by reacting a dialkyluracil, e.g. 1,3-dimethyluracil, with a compound of formula $Cy^1 L^1 (Alk^1)_n NHC(S)CH_2CN$, which reaction may conveniently be accomplished in the presence of a base, e.g. sodium methoxide, typically in an alkanol solvent, for example a methanol/ethanol mixture; the 3-cyano-6-oxo-1,6-dihydropyridine-2-thiolate intermediate thereby obtained can then be transformed into the desired precursor compound referred to above by treatment with a compound of formula Hal-CH$_2$—R$^{10}$ [in which Hal represents a halogen atom, e.g. chloro or bromo, and —C(R$^{10}$)= corresponds to the moiety Y as defined above], typically in a solvent such as acetonitrile or ethanol.

In another process according to the invention, a compound of formula (1) in which A is a —C(R$^b$)= group, X is an —O— or —S— atom or a —NH— group and Y is a —C(CN)= group may be prepared using the reactions set out in Scheme 2 below:

N,N-dimethylformamide at a temperature from around 0° C. to 110C. Amides of formula (10) may be obtained from the corresponding acids of formula (11) using conventional procedures, for example by reaction with 1,1'-carbonyldiimidazole and aqueous ammonia in a solvent such as N,N-dimethylformamide at ambient temperature. The intermediate acids of formula (11) may be prepared by hydrolysis of esters of formula (4) using a base such as lithium hydroxide in water and a solvent such as tetrahydrofuran.

Compounds of formula (1) in which A is a —N= atom may be obtained using the synthetic routes in Schemes (1) and (2) with a pyrimidine starting material of formula (12):

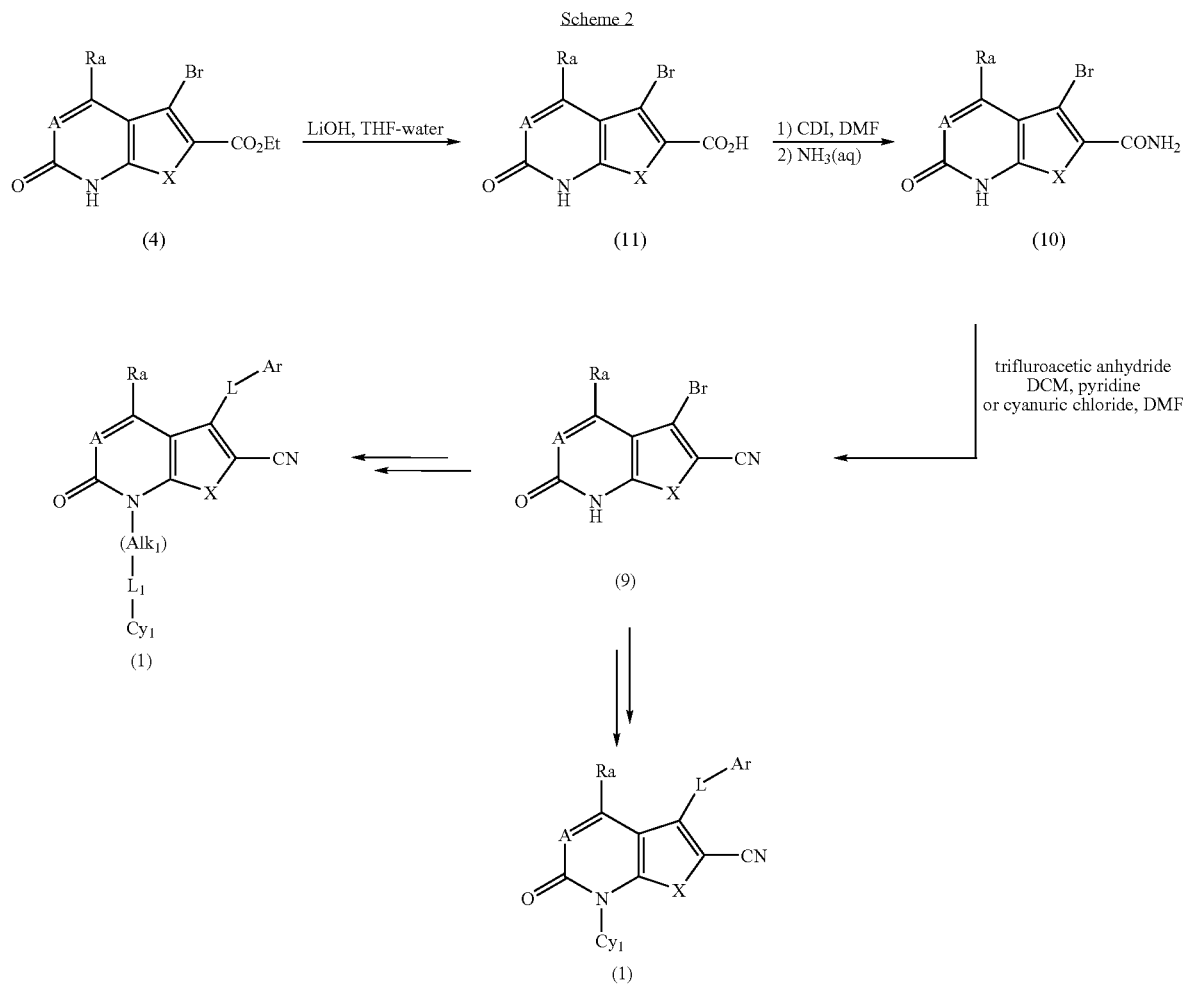

Thus, in Scheme 2, a 2-cyano intermediate of formula (9) may be converted in a final step to a compound of the invention using the reactions and reagents described above in relation to the conversion of intermediates of formula (4) to compounds of the invention. Nitriles of formula (9) may be obtained by dehydration of the corresponding amide of formula (10) using a dehydrating agent such as trifluoroacetic anhydride in the presence of a base such as pyridine in a solvent, for example a halogenated hydrocarbon such as dichloromethane, at around ambient temperature. Alternatively, cyanuric chloride may be used in a solvent such as

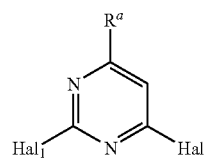

wherein Hal$_1$ and Hal, which may be the same or different, is each a halogen atom such as a chlorine atom.

In this instance the final step in the synthesis of a compound of the invention may be hydrolysis of the $Hal_1$ atom using a base such as sodium hydroxide or potassium hydroxide in a solvent such as an alcohol, e.g. methanol or ethanol, at an elevated temperature, e.g. the reflux temperature. Alternatively, the $Hal_1$ atom may first be converted to an ether by reaction with an alkoxide such as sodium methoxide or sodium benzyloxide in a solvent, e.g. an alcohol such as methanol or ethanol, at a temperature between 0° C. and the reflux temperature, and the ether then cleaved using standard procedures such as by reduction with hydrogen gas in the presence of a catalyst such as a palladium catalyst, e.g. palladium on charcoal, or, where the ether is an alkyl ether, by reaction with a trialkylsilyl halide such as trimethylsilyl chloride, optionally in the presence of an inorganic halide such as sodium iodide in a solvent such as a halogenated hydrocarbon, e.g. dichloromethane, or in a nitrile, e.g. acetonitrile.

Compounds of the invention and intermediates thereto where A represents a —N($R^b$)— or —C($R^b$)($R^c$)— group may be generated from corresponding compounds of the invention or intermediates thereto where A represents a —N= or —C($R^b$)= group by reduction, for instance by catalytic hydrogenation using a metal catalyst such as palladium on charcoal in the presence of hydrogen gas at an elevated pressure in a solvent such as an alcohol, e.g. ethanol, optionally at an elevated temperature, e.g. between 40° C. and 60° C.

Where in the general processes described above intermediates such as alkylating agents of formula $Cy^1L^1(Alk^1)_nZ$, reagents of formula $HXCH_2CO_2Et$ and any other intermediates required in the synthesis of compounds of the invention are not available commercially or known in the literature, they may be readily obtained from simpler known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other intermediates and in particular compounds of formula (1) where appropriate functional groups exist in these compounds.

Thus, for example, aromatic halogen substituents in the compounds may be subjected to halogen-metal exchange with a base, for example a lithium base such as n-butyllithium or tert-butyllithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile; a thiomethyl group may be introduced by using dimethyldisulphide as the electrophile, an alcohol group may be introduced by using an aldehyde as the electrophile, and an acid may be introduced by using carbon dioxide as the electrophile. Aromatic acids of formula $ArCO_2H$ may also be generated by quenching Grignard reagents of formula ArMgHal with carbon dioxide.

Aromatic acids of formula $ArCO_2H$ generated by this method and acid-containing compounds in general may be converted to activated derivatives, e.g. acid halides, by reaction with a halogenating agent such as a thionyl halide, e.g. thionyl chloride, a phosphorus trihalide such as phosphorus trichloride, or a phosphorus pentahalide such as phosphorus pentachloride, optionally in an inert solvent such as an aromatic hydrocarbon, e.g. toluene, or a chlorinated hydrocarbon, e.g. dichloromethane, at a temperature from about 0° C. to the reflux temperature, or may be converted into Weinreb amides of formula ArC(O)N(OMe)Me by conversion to the acid halide as just described and subsequent reaction with an amine of formula HN(OMe)Me or a salt thereof, optionally in the presence of a base such as an organic amine, e.g. triethylamine, in an inert solvent such as an aromatic hydrocarbon, e.g. toluene, or a chlorinated hydrocarbon, e.g. dichloromethane, at a temperature from about 0° C. to ambient temperature.

Acid (—$CO_2H$) groups in the compounds of the invention or intermediates thereto may be transformed into amide (—$CONH_2$) groups by treatment with ammonia in the presence of a condensing agent, for example 1,1'-carbonyldiimidazole, typically in a solvent such as N,N-dimethylformamide.

Compounds of the invention and intermediates thereto may be prepared by alkylation, arylation or heteroarylation. For example, compounds containing a -$L^1$H group (where $L^1$ is a linker atom or group) may be treated with an alkylating agent $Cy^1Z^2$ in which $Z^2$ is a leaving atom or group such as a halogen atom, e.g. a fluorine, chlorine, bromine or iodine atom, or a sulphonyloxy group such as an alkylsulphonyloxy, e.g. trifluoromethylsulphonyloxy, or arylsulphonyloxy, e.g. p-toluenesulphonyloxy, group.

The reaction may be carried out in the presence of a base such as a carbonate, e.g. caesium carbonate or potassium carbonate, an alkoxide, e.g. potassium tert-butoxide, or a hydride, e.g. sodium hydride, in a dipolar aprotic solvent such as an amide, e.g. a substituted amide such as N,N-dimethylformamide, or an ether, e.g. a cyclic ether such as tetrahydrofuran.

In another example, compounds containing a -$L^2$H group as defined above may be functionalised by acylation or thioacylation, for example by reaction with the alkylating agents just described but in which $Z^2$ is replaced by a —C(O)$Z^3$, —C(S)$Z^3$, —N($R^2$)C(O)$Z^3$ or —N($R^2$)C(S)$Z^3$ group in which $Z^3$ is a leaving atom or group as described for $Z^2$. The reaction may be performed in the presence of a base, such as a hydride, e.g. sodium hydride, or an amine, e.g. triethylamine or N-methylmorpholine, in a solvent such as a halogenated hydrocarbon, e.g. dichloromethane or carbon tetrachloride, or an amide, e.g. N,N-dimethylformamide, at for example ambient temperature. Alternatively, the acylation may be carried out under the same conditions with an acid (for example one of the alkylating agents described above in which $Z^2$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, or a benzotriazole such as O-(7-azabenzotriazol-1-yl)-N,N,N',N'-tetramethyluronium hexafluorophosphate, advantageously in the presence of a catalyst such as a N-hydroxy compound, e.g. a N-hydroxytriazole such as 1-hydroxybenzotriazole. Alternatively, the acid may be reacted with a chloroformate, for example ethyl chloroformate, prior to the desired acylation reaction In a further example, compounds may be obtained by sulphonylation of a compound containing an —OH group by reaction with one of the above alkylating agents but in which $Z^2$ is replaced by a —S(O)Hal or —$SO_2$Hal group (in which Hal is a halogen atom such as chlorine atom) in the presence of a base, for example an inorganic base such as sodium hydride, in a solvent such as an amide, e.g. a substituted amide such as N,N-dimethylformamide, at for example ambient temperature.

In another example, compounds containing a -$L^2$H group as defined above may be coupled with one of the alkylation agents just described but in which $Z^2$ is replaced by an —OH group in a solvent such as tetrahydrofuran in the presence of a phosphine, e.g. triphenylphosphine, and an activator such as diethyl, diisopropyl or dimethyl azodicarboxylate.

Ester groups such as —$CO_2Alk^6$ and —$CO_2R^4$ in the compounds of formula (1) and intermediates thereto may be converted to the corresponding acid (—$CO_2H$) by acid- or base-catalysed hydrolysis depending on the nature of the group $Alk^6$ or $R^4$. Acid- or base-catalysed hydrolysis may be achieved, for example, by treatment with an organic or inorganic acid, e.g. trifluoroacetic acid, in an organic solvent, e.g. dichloromethane, or a mineral acid such as hydrochloric acid in a solvent such as 1,4-dioxane, or an alkali metal hydroxide, e.g. lithium hydroxide or sodium hydroxide, in an aqueous alcohol, e.g. aqueous methanol or aqueous ethanol.

In a further example, —$OR^6$ (where $R^6$ represents an alkyl group such as methyl) in compounds of formula (1) and intermediates thereto may be cleaved to the corresponding alcohol —OH by reaction with boron tribromide in a solvent such as a halogenated hydrocarbon, e.g. dichloromethane, at a low temperature, e.g. around −78° C.

Alcohol (—OH) groups may also be obtained by hydrogenation of a corresponding —$OCH_2R^{31}$ group (where $R^{31}$ is an aryl group) using a metal catalyst, for example palladium on a support such as carbon, in a solvent such as ethanol in the presence of ammonium formate, cyclohexadiene or hydrogen, from around ambient temperature to the reflux temperature. In another example, —OH groups may be generated from the corresponding ester (e.g. —$CO_2Alk^6$) or aldehyde (—CHO) by reduction, using for example a complex metal hydride such as lithium aluminium hydride or sodium borohydride in a solvent such as methanol.

In another example, —OH groups in the compounds may be converted to a corresponding —$OR^6$ group by coupling with a reagent $R^6OH$ in a solvent such as tetrahydrofuran in the presence of a phosphine, e.g. triphenylphosphine and an activator such as diethyl, diisopropyl or dimethyl azodicarboxylate.

Aminosulphonylamino (—$NHSO_2NH_2$) groups in the compounds may be obtained, in another example, by reaction of a corresponding amine (—$NH_2$) with sulphamide in the presence of an organic base such as pyridine at an elevated temperature, e.g. the reflux temperature.

In another example, compounds containing a —$NHCSR^7$ or —$CSNHR^7$ group may be prepared by treating a corresponding compound containing a —$NHCOR^7$ or —$CONHR^7$ group with a thiation reagent, such as Lawesson's Reagent or $P_2S_5$, in an anhydrous solvent, for example a cyclic ether such as tetrahydrofuran, at an elevated temperature such as the reflux temperature.

In a further example, amine (—$NH_2$) groups may be alkylated using a reductive alkylation process employing an aldehyde and a reducing agent. Suitable reducing agents include borohydrides, for example sodium triacetoxyborohydride or sodium cyanoborohydride. The reduction may be carried out in a solvent such as a halogenated hydrocarbon, e.g. dichloromethane, a ketone such as acetone, or an alcohol, e.g. ethanol, where necessary in the presence of an acid such as acetic acid at around ambient temperature. Alternatively, the amine and aldehyde may be initially reacted in a solvent such as an aromatic hydrocarbon, e.g. toluene, and then subjected to hydrogenation in the presence of a metal catalyst, for example palladium on a support such as carbon, in a solvent such as an alcohol, e.g. ethanol.

Amine (—$NH_2$) groups in the compounds of the invention or intermediates thereto may generally be transformed into halogen atoms, e.g. bromo, by treatment with a nitrite reagent, e.g. tert-butyl nitrite, in the presence of a copper(II) halide, e.g. copper(II) bromide, typically in a solvent such as acetonitrile.

In a further example, amine (—$NH_2$) groups in compounds of formula (1) and intermediates thereto may be obtained by hydrolysis from a corresponding imide by reaction with hydrazine in a solvent such as an alcohol, e.g. ethanol, at ambient temperature.

In another example, a nitro (—$NO_2$) group may be reduced to an amine (—$NH_2$), for example by catalytic hydrogenation using for example hydrogen in the presence of a metal catalyst, for example palladium on a support such as carbon, in a solvent such as an ether, e.g. tetrahydrofuran, or an alcohol, e.g. methanol, or by chemical reduction using for example a metal, e.g. tin or iron, in the presence of an acid such as hydrochloric acid.

In a further example, amine (—$CH_2NH_2$) groups in compounds of formula (1) and intermediates thereto may be obtained by reduction of nitriles (—CN), for example by catalytic hydrogenation using for example hydrogen in the presence of a metal catalyst, for example palladium on a support such as carbon, or Raney® nickel, in a solvent such as an ether, e.g. a cyclic ether such as tetrahydrofuran, or an alcohol, e.g. methanol or ethanol, optionally in the presence of ammonia solution at a temperature from ambient temperature to the reflux temperature, or by chemical reduction using for example a metal hydride, e.g. lithium aluminium hydride, in a solvent such as an ether, e.g. a cyclic ether such as tetrahydrofuran, at a temperature from 0° C. to the reflux temperature.

In another example, sulphur atoms in the compounds, for example when present in a group L, $L^1$ or $L^2$, may be oxidised to the corresponding sulphoxide or sulphone using an oxidising agent such as a peroxyacid, e.g. 3-chloroperoxybenzoic acid, in an inert solvent such as a halogenated hydrocarbon, e.g. dichloromethane, at around ambient temperature.

In a further example, N-oxides of compounds of formula (1) may in general be prepared for example by oxidation of the corresponding nitrogen base as described above in relation to the preparation of intermediates of formula (5).

Salts of compounds of formula (1) may be prepared by reaction of compounds of formula (1) with an appropriate base in a suitable solvent or mixture of solvents, e.g. an organic solvent such as an ether, e.g. diethyl ether, or an alcohol, e.g. ethanol, using conventional procedures.

Where it is desired to obtain a particular enantiomer of a compound of formula (1) this may be produced from a corresponding mixture of enantiomers using any suitable conventional procedure for resolving enantiomers.

Thus, for example, diastereomeric derivatives, e.g. salts, may be produced by reaction of a mixture of enantiomers of formula (1), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt.

In another resolution process a racemate of formula (1) may be separated using chiral High Performance Liquid Chromatography. Alternatively, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the invention. All temperatures are in ° C. The following abbreviations are used:
NMM—N-methylmorpholine;
MeOH—methanol;
DCM—dichloromethane;
DIPEA—diisopropylethylamine;
Pyr—pyridine;
DMSO—dimethylsulphoxide;
Et$_2$O—diethyl ether;
THF—tetrahydrofuran;
MCPBA—3-chloroperoxybenzoic acid;
FMOC—9-fluorenylmethoxycarbonyl;
DBU—1,8-diazabicyclo[5.4.0]undec-7-ene;
CDI—1,1'-carbonyldiimidazole; DMAP—4-(dimethylamino)pyridine;
EDC—1-[3-(dimethylamino)propyl]-3-ethylcarbodiimide hydrochloride;
HOBT—1-hydroxybenzotriazolehydrate;
BINAP—2,2'-bis(diphenylphosphino)-1,1'-binaphthyl;
DMF—N,N-dimethylformamide;
DME—ethylene glycol dimethyl ether;
EtOAc—ethyl acetate;
BOC—tert-butoxycarbonyl;
AcOH—acetic acid;
EtOH—ethanol;
Ar—aryl;
iPr—isopropyl;
Me—methyl;
h—hour;
NBS—N-bromosuccinimide;
r.t.—room temperature;
MTBE—tert-butyl methyl ether.

All NMRs were obtained either at 300 MHz or 400 MHz.

Compounds were named with the aid of either Beilstein Autonom, supplied by MDL Information Systems GmbH, Theodor-Heuss-Allee 108, D-60486 Frankfurt, Germany, or ACD Labs Name (v. 5.0 or v. 6.0), supplied by Advanced Chemical Development, Toronto, Canada.

LCMS retention times (RT) quoted were generated on a Hewlett Packard 1100 LC/MS using the following method: Phenomenex Luna 3µC$_{18}$(2) 50×4.6 mm column; mobile phase A=0.1% formic acid in water; mobile phase B=0.1% formic acid in MeCN; flow rate of 0.9 mlmin$^{-1}$; column temperature 40° C.
Gradient:

| Time (min) | % B |
|---|---|
| Initial | 5 |
| 2.0 | 95 |
| 3.0 | 95 |
| 5.0 | 5 |
| 5.5 | end |

Where stated, alternative LCMS conditions (Conditions B) were used:

LCMS retention times (RT) quoted were generated on a Hewlett Packard 1100/ThermoFinnigan LCQ Duo LC/MS system using Electrospray ionisation and the following LC method: Phenomenex Luna C$_{18}$(2) 5µ 100 mm×4.6 mm column; mobile phase A=0.08% formic acid in water; mobile phase B=0.08% formic acid in MeCN; flow rate of 3.0 mlmin$^{-1}$; column temperature 35° C.
Gradient:

| Time (min) | % A | % B |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Intermediate 1

Ethel 3-aminothieno[2,3-b]pyridine-2-carboxylate

A mixture of 2-chloro-3-cyanopyridine (330 g), ethyl 2-mercaptoacetate (361.2 g), sodium carbonate (265 g) and EtOH (1.2 l) was heated to reflux for 4.5 hours. It was then cooled to ambient temperature, added to water (10 l) and the addition was washed with water (5 l). The resulting slurry was stirred for 30 minutes and then it was filtered. The filter cake was washed with two portions of water (2×2.5 l) and dried at the pump. The solids were then dried to constant weight under vacuum at 45° C. to yield the title compound as a brown solid (493.1 g, 93.2%). δ$_H$ (CDCl$_3$) 8.68 (1H, dd, J 4.7, 1.2 Hz), 7.93 (1H, dd, J 8.5, 1.2 Hz), 7.29 (1H, dd, J 8.5, 4.7 Hz), 5.90 (2H, b), 4.38 (2H, q, J 7.0 Hz), 1.40 (3H, t, J 7.0 Hz). LCMS RT 2.9 minutes, 223 (M+H)$^+$.

Intermediate 2

Ethyl 3-bromothieno[2,3-]pyridine-2-carboxylate

Intermediate 1 (363.6 g) was added in portions over two hours to a mixture of copper(II) bromide (403.3 g), tert-butyl nitrite (220.6 g) and acetonitrile (3.6 l) stirred at a temperature of 20 to 25° C. The mixture was stirred at 20° C. for 2 hours before it was slowly added to 2M HCl(aq) (4.2 l). The reaction mixture slurry was filtered and the solids were washed with water (500 ml). The combined filtrate was extracted with ethyl acetate (8 l), and this ethyl acetate solution was washed with 2M HCl(aq) (2.2L). The solids were dissolved in ethyl acetate (6 l), and this solution was washed twice with 2M HCl(aq) (4.4 l and 2.2 l). The two ethyl acetate solutions were then combined and washed with 2M HCl(aq) (2.2 l) and twice with water (2×2 l). The ethyl acetate solution was then dried (NgSO$_4$), filtered and concentrated in vacuo at 40 mbar and 60° C. to give a solid residue. This was broken up and dried to constant weight under vacuum at 45° C. to yield the title compound as a brown solid (458.5 g, 97.9%). δ$_H$ DMSO-d$_6$) 8.89 (1H, d, J 4.7 Hz), 8.47 (1H, d, J 8.6 Hz), 7.71 (1H, dd, J 8.6, 4.7 Hz), 4.46 (2H, q, J 7.2 Hz), 1.40 (3H, t, J 7.2 Hz). LCMS RT 3.8 minutes, 288 (M+H)$^+$.

Intermediate 3

Ethyl 3-Bromothieno[2,3-b]pyridine-2-carboxylate N-oxide

To a slurry of Intermediate 2 (214 g, 0.747 mol) in DCM (2140 ml) under nitrogen was added MCPBA (240 g @ 70%=168 g, 0.97 mol) portionwise over 0.5 h. The reaction was then stirred at room temperature for 18 h. The reaction mixture was quenched with water (800 ml) and the pH adjusted to 8.5 with 10% w/v sodium carbonate solution (1250 ml). The basic aqueous layer was removed and the organic layer washed with water until pH 7. The organic layer was concentrated in vacuo and the crude title product was recovered as a tan solid. The crude product was purified by slurrying in MTBE (600 ml) for 1 h at 0-5° C. to give the title compound (174 g, 77%). $\delta_H$ (CDCl$_3$) 8.44 (1H, dd, J 6.2, 0.8 Hz), 7.87 (1H, dd, J 8.3, 0.8 Hz), 7.48 (1H, dd, J 8.3, 6.2 Hz), 4.49 (2H, q, J 7.1 Hz), 1.48 (3H, t, J 7.1 Hz). LCMS (ES$^+$) RT 2.61 minutes, 302 (M+H)$^+$.

Intermediate 4

Ethyl 3-bromo-6-oxo-6,7-dihdrothieno[2,3-b]pyridine-2-carboxylate

A mixture of Intermediate 3 (500 mg, 1.66 mmol) and DMF (10 ml) was set to stir at 0° C. under nitrogen. To this reaction mixture was added trifluoroacetic anhydride (3.49 g, 2.36 ml, 16.6 mmol) in one portion via syringe. After stirring for 16 hours the volatiles were removed in vacuo and the residue co-evaporated with toluene (2×20 ml). The crude material was then extracted with EtOAc (2×100 ml). The EtOAc extracts were dried (MgSO$_4$) and concentrated in vacuo. The crude product was purified by a re-slurry in toluene (10 ml) to give the title compound as a beige solid (260 mg, 52%). $\delta_H$ (DMSO-d$_6$) 12.20 (1H, br s), 7.75 (1H, d, J 9.0 Hz), 6.50 (1H, d, J 9.0 Hz), 4.15 (2H, q, J 7.1 Hz), 1.12 (3H, t, J 7.1 Hz). LCMS (ES$^+$) RT 2.86 minutes, 302 ((M+H)$^+$, 100%). MP=261.7-268.1° C.

Intermediate 5

Ethel 3-bromo-6-oxo-7-phenyl-6,7-dihydrothieno[2,3-b]pyridine-2-carboxylate

To a 2-necked round-bottomed flask was added in sequence Intermediate 4 (302 mg, 1.00 mmol), copper(II) acetate (278 mg, 1.50 mmol), phenylboronic acid (488 mg, 4.00 mmol), DCM (5 ml) and pyridine (158 mg, 2.00 mmol). The reaction was stirred at room temperature for 18 h with the exclusion of moisture. The reaction was then diluted with DCM (50 ml), washed with 2M HCl(aq) (50 ml), and the aqueous was re-extracted with DCM (50 ml). The combined organics were then washed with water (50 ml), dried (MgSO$_4$) and concentrated in vacuo. The crude product was purified by a slurry in methanol (12 ml), to give the title compound as a beige solid (270 mg, 72%). $\delta_H$ (CDCl$_3$) 7.82 (1H, d, J 8.5 Hz), 7.70-7.62 (3H, m), 7.54-7.42 (2H, m), 6.70 (1H, d, J 8.5 Hz), 4.15 (2H, q, J 7.1 Hz), 1.14 (3H, t, J 7.1 Hz). LCMS (ES$^+$) RT 3.75 minutes, 378 (M+H)$^+$. MP=201.6-206.0° C.

Intermediate 6

Sodium 3-cyano-6-oxo-1-phenyl-1,6-dihydropyridine-2-thiolate

A solution of sodium methoxide in MeOH (30 wt %, 202.2 g) was added to absolute EtOH (360 ml), followed by 1,3-dimethyluracil (75 g) and 2-cyano-N-phenylthioacetamide (Adhikari et al., *Australian J. Chem.*, 1999, 52, 63-67) (90 g). The resulting mixture was heated at reflux for 8 h and then allowed to cool to ambient temperature overnight. The reaction mixture was then cooled to +5° C. and maintained at this temperature for at least an hour when the product was recovered by filtration. The filter cake was washed with cold (+5° C.) absolute ethanol (450 ml) and then dried to constant weight under vacuum at 45° C. to give the title compound as a pale pink solid (130.0 g). The product thus obtained contained residual EtOH and MeOH, estimated at 12.2 wt % by $^1$H nmr, corresponding to a corrected yield of 114.1 g. $\delta_H$ (DMSO-d$_6$) 7.32 (2H, m), 7.27-7.18 (1H, m), 7.16 (1H, d, J 9.1 Hz), 6.92 (2H, m), 5.63 (1H, d, J 9.1 Hz). LCMS (Conditions B) (ES$^+$) RT 2.43 minutes, 229 (M+H)$^+$.

Intermediate 7

3-Amino-6-oxo-7-phenyl-6,7-dihydrothieno[2,3-b]pyridine-2-carbonitrile

A mixture of Intermediate 6 (100 g at 100%) and chloroacetonitrile (30.4 ml) in acetonitrile (500 ml) was heated at reflux for 2 h. The mixture was cooled, initially to 40° C. when water (300 ml) was added, and then to +10° C. The reaction was maintained at +10° C. for at least 1 h when the product was recovered by filtration. The filter cake was washed with cold (+10° C.) water (500 ml) followed by a cold (+10° C.) mixture of acetonitrile and water (1:1, 300 ml). The product was dried under vacuum at 50° C. to constant weight to give the title compound as an off-white solid (100.9 g). $\delta_H$ (DMSO-d$_6$) 7.90 (1H, d, J 9.6 Hz), 7.46-7.33 (3H, m), 7.25 (2H, m), 6.95 (2H, br s), 6.35 (1H, d, J 9.6 Hz). LCMS (Conditions B) (ES$^+$) RT 2.69 minutes, 268 (M+H)$^+$.

Intermediate 8

3-Amino-6-oxo-7-phenyl-6,7-dihydrothieno[2,3-b]pyridine-2-carboxylic acid ethyl ester A mixture of Intermediate 6 (0.34 g at 100%) and ethyl bromoacetate (0.197 ml) in ethanol (6 ml) was stirred at room temperature for 1 h. Water (10 ml) was then added. The solid was filtered and washed with more water (2 ml). The product was dried under vacuum at 40° C. to constant weight to give the title compound as a pale pink solid (0.35 g). $\delta_H$ (DMSO-d$_6$) 8.2 (1H, d, J 9.6 Hz), 7.6 (3H, m), 7.45 (2H, m), 7.15 (2H, br s), 6.55 (1H, d, J 9.6 Hz), 4.15 (2H, q, J 7.1 Hz), 1.2 (3H, t, J 7.1 Hz). LCMS (Conditions B) (ES$^+$) RT 3.29 minutes, 315 (M+H)$^+$.

Intermediate 9

3-Bromo-6-oxo-7-phenyl-6,7-dihydrothieno[2,3-b]pyridine-2-carbonitrile

To a mixture of anhydrous copper(II) bromide (23.4 g) and tert-butyl nitrite (14.8 ml) in acetonitrile (600 ml), at room temperature, was added Intermediate 7 (20 g) portionwise, at such a rate as to keep the internal temperature below 25° C. The addition took approximately 1 hour. Analysis by HPLC indicated almost complete conversion of starting material after a further 30 minutes of stirring. The reaction mixture was then poured onto 500 ml of 1M HCl (N.B. caution, brown fumes given off). This was then extracted with dichloromethane (2×400 ml). The combined organic extracts were then washed with 1M HCl (3×300 ml), dried over MgSO$_4$ and evaporated to dryness. The resulting crude product was then recrystallised from methyl isobutyl ketone (700 ml). The product was dried under vacuum at 50° C. to constant weight to give the title compound as a light brown solid (15.14 g). $\delta_H$ (CDCl$_3$) 7.75 (1H, d, J 8.5 Hz), 7.55-7.70 (3H, m), 7.35 (2H, m), 6.80 (1H, d, J 8.5 Hz). LCMS (Conditions B) (ES$^+$) RT 3.54 minutes, no parent ion observed.

Intermediate 10

3-Bromo-6-oxo-7-phenyl-6,7-dihydrothieno[2,3-b]pyridine-2-carboxylic acid

Sodium hydroxide (1.83 g, 45.8 mmol, 1.1 equiv.) was added to a suspension of Intermediate 5 (15.75 g, 41.6 mmol, 1.0 equiv.) in ethanol (78 ml) and water (78 ml) at room temperature. The reaction mixture was then heated to reflux. Once reflux was attained the solid material had gone into solution and analysis by HPLC indicated complete conversion to the acid. The reaction mixture was then cooled to ~70° C. and c. hydrochloric acid (46 ml) added over a 10 minute period. The reaction was allowed to cool to room temperature and the resultant solid collected by filtration, washed with water (3×25 ml) and dried in vacuo to give the title compound as a beige solid (13.81 g, 97%). $\delta_H$ (DMSO-$d_6$) 8.13 (1H, d, J 9.6 Hz), 7.92-7.80 (3H, m), 7.78-7.74 (2H, m), 6.92 (1H, d, J 9.6 Hz).

Intermediate 11

3-Bromo-6-oxo-7-phenyl-6,7-dihydrothieno[2,3-b]pyridine-2-carboxamide

CDI (530 mg, 3.27 mmol) was added to a solution of Intermediate 10 (800 mg, 2.29 mmol) in DMF (15 ml). After 10 min, ammonia (25% solution) (5 ml) was added and the reaction mixture stirred at r.t. for 4 h. The solvent was removed in vacuo and the residue acidified with 2M HCl and extracted with DCM (×3). The combined organic extracts were dried ($Na_2SO_4$) and concentrated in vacuo to give the title compound as a white solid (600 mg, 75%). $\delta_H$ (DMSO-$d_6$) 6.67 (1H, d, J 9.6 Hz), 7.7-7.5 (5H, m), 7.85 (1H, d. J 9.6 Hz). LCMS (ES$^+$) RT 2.69 minutes, 349 (M+H)$^+$.

Intermediate 12

Ethyl 6-oxo-7-phenyl-3-(phenylethynyl)-6,7-dihydrothieno[2,3-b]pyridine-2-carboxylate A mixture of Intermediate 5 (756 mg, 2.0 mmol), dichlorobis(triphenyl-phosphine)palladium(II) (140 mg, 0.2 mmol) and Cu(I)I (190 mg, 1.0 mmol) was suspended in DME (10 ml) and diisopropylethylamine (1.5 ml, 10 mmol) added. Phenylacetylene (0.33 ml, 3.2 mmol) was added dropwise and the black solution heated at 75° C. for 18 h. The reaction mixture was cooled to r.t., and the solvents removed in vacuo. The crude residue was purified by chromatography on silica (0-20% EtOAc in hexanes) to give the title compound as a white solid (430 mg, 54%). $\delta_H$ (CDCl$_3$) 7.95 (1H, d, J 9.5 Hz), 7.60-7.49 (5H, m), 7.37-7.31 (5H, m), 6.67 (1H, d, J 9.5 Hz), 4.28 (2H, q, J 7.2 Hz), 1.29 (3H, t, J 7.2 Hz). LCMS (ES$^+$) RT 4.15 minutes, 400 (M+H)$^+$.

Intermediate 13

Ethyl 3-bromo-7-(cyclopropylmethyl)-6-oxo-6,7-dihydrothieno[2,3-b]pyridine-2-carboxylate Sodium hydride (60% in mineral oil) (3.27 g, 81.4 mmol) was added in portions to a solution of Intermediate 4 (22.3 g, 74 mmol) in DMF (300 ml) at 0° C. The mixture was stirred at r.t. for 30 min then cyclopropylmethyl bromide (10 g, 74 mmol) was added slowly and the mixture heated at 60° C. overnight. The DMF was removed in vacuo and the residue partitioned between EtOAc and brine. The organic phase was dried MgSO$_4$) and concentrated in vacuo. Purification by column chromatography (silica, 0% to 10% EtOAc in DCM) gave the title compound as a yellow solid (12.5 g, 47%). $\delta_H$ (CDCl$_3$) 7.57 (1H, d, J 9.5 Hz), 6.47 (1H, d, J 9.5 Hz), 4.22 (2H, q, J 7.0 Hz), 3.87 (2H, d, J 7.1 Hz), 1.26-1.19 (4H, m), 0.43-0.37 (4H, m). LCMS (ES$^+$) RT 3.80 minutes, 357 (M+H)$^+$.

EXAMPLE 1

Ethyl 3-(benzylamino)-6-oxo-7-phenyl-6,7-dihydrothieno[2,3-b]pyridine-2-carboxylate Tris(dibenzylideneacetone)dipalladium(0) (12 mg, 0.0133 mmol, 5 mol %) was added to a mixture of Intermediate 5 (100 mg, 0.265 mmol), caesium carbonate (120 mg, 0.37 mmol), benzylamine (0.035 ml, 0.32 mmol) and BINAP (17 mg, 0.027 mmol, 10 mol %) in anhydrous toluene (2 ml) and the reaction heated to reflux under nitrogen for 18 h. Solvent was removed in vacuo and the crude residue purified by chromatography on silica (0-20% EtOAc in DCM) to give the title compound as a white solid (52 mg). $\delta_H$ (CDCl$_3$) 7.80 (1H, br s), 7.72 (1H, d, J 9.9 Hz), 7.60-7.48 (3H, m), 7.28-7.10 (7H, m), 6.37 (1H, d, J 9.9 Hz), 4.73 (2H, br d, J 4.5 Hz), 4.14 (2H, q, J 7.1 Hz), 1.18 (3H, t, J 7.1 Hz). LCMS (ES$^+$) RT 4.03 minutes, 405 (M+H)$^+$.

EXAMPLES 2 TO 4

General Procedure for the Preparation of ethyl 3-benzylamino-6-oxo-7-phenyl-6,7-dihydrothieno[2,3-b]pyridine-2-carboxylates The compounds of Examples 2-4 were prepared by parallel synthesis using a Radleys Carousel reaction station (Radleys Ltd., Saffron Walden, U.K.) following a procedure similar to that described for Example 1. Therefore, to each oven dried reaction tube in the Carousel was added a magnetic stirrer, the appropriate substituted aniline or benzylamine (0.64 mmol), anhydrous toluene (3 ml), Intermediate 5 (200 mg, 0.53 mmol), caesium carbonate (240 mg, 0.74 mmol) and tris(dibenzylideneacetone)dipalladium(0) (48 mg, 0.053 mmol, 10 mol %). The reactions were heated to reflux under nitrogen and with magnetic stirring for 48 h. Each reaction was then diluted with DCM (10 ml), washed with water (10 ml), dried (MgSO$_4$) and concentrated in vacuo. The crude products were purified on silica eluting with 0-20% EtOAc in DCM to give the title compounds as solids.

EXAMPLE 2

Ethyl 3-(N-benzyl-N-methylamino)-6-oxo-7-phenyl-6,7-dihydrothieno[2,3-b]pyridine-2-carboxylate From N-benzylmethylamine to give the title compound (95 mg). $\delta_H$ (CDCl$_3$) 7.73 (1H, d, J 9.6 Hz), 7.58-7.41 (3H, m), 7.36-7.14 (7H, m), 6.52 (1H, d, J 9.6 Hz), 4.43 (2H, s), 4.17 (2H, q, J 7.1 Hz), 2.89 (3H, s), 1.21 (3H, t, J 7.1 Hz). LCMS (ES$^+$) RT 4.19 minutes, 419 (M+H)$^+$.

EXAMPLE 3

Ethyl 6-oxo-7-phenyl-3-[(1-phenylethyl)amino]-6,7-dihydrothieno[2,3-b]pyridine-2-carboxylate From α-methylbenzylamine to give the title compound (149 mg). $\delta_H$ (CDCl$_3$) 7.83 (1H, bd, J 7.6 Hz), 7.58 (1H, d, J 9.9 Hz), 7.54-7.36 (3H, m), 7.32-7.14 (7H, m), 6.27 (1H, d, J 9.9 Hz), 4.98 (1H, quintet, J 6.8 Hz), 4.18 (2H, q, J 7.1 Hz), 1.58 (3H, d, J 6.8 Hz), 1.21 (3H, t, J 7.1 Hz). LCMS (ES$^+$) RT 4.19 minutes, 419 (M+H)$^+$.

EXAMPLE 4

Ethyl 3-[(2,6-difluorobenzyl)amino]-6-oxo-7-phenyl-6,7-dihydrothieno[2,3-b]pyridine-2-carboxylate From 2,6-difluorobenzylamine to give the title compound (130 mg). $\delta_H$ (CDCl$_3$) 8.04 (1H, d, J 9.9 Hz), 7.61-7.40 (3H, m), 7.39-7.25 (3H, m), 7.38-7.14 (1H, m), 6.93-6.78 (2H, m), 6.54 (1H, d, J 9.9 Hz), 4.73 (2H, d, J 6.0 Hz), 4.10 (2H, q, J 7.1 Hz), 1.15 (3H, t, J 7.1 Hz). LCMS (ES$^+$) RT 3.98 minutes, 441 (M+H)$^+$.

EXAMPLE 5

Ethyl 3-benzyl-6-oxo-7-phenyl-6,7-dihydrothieno[2,3-b]pyridine-2-carboxylate

Benzyl bromide (0.040 ml, 0.317 mmol) was added to activated zinc powder (26 mg, 0.397 mmol) in anhydrous THF (2 ml) under nitrogen and the mixture heated to reflux for 2 h. The reaction was cooled to r.t. and Intermediate 5 (100 mg, 0.265 mmol) and tetrakis(triphenylphosphine)palladium (0) (30 mg, 0.026 mmol, 10 mol %) added to the reaction mixture. The reaction was then heated to reflux for 18 h with two further portions of Pd(PPh$_3$)$_4$ (30 mg) added at intervals during the reaction. The reaction was partitioned between EtOAc and water and the EtOAc extracts dried (MgSO$_4$) and concentrated in vacuo. The crude product was purified by chromatography on silica (0-20% EtOAc in DCM) to give the title compound as a white solid (87 mg). $\delta_H$ (CDCl$_3$) 7.69 (1H, d, J 9.6 Hz), 7.67-7.30 (3H, m), 7.25-7.18 (2H, m), 7.20-7.00 (5H, m), 6.51 (1H, d, J 9.6 Hz), 4.51 (2H, s), 4.21 (2H, q, J 7.2 Hz), 1.22 (3H, t, J 7.2 Hz). LCMS (ES) RT 3.92 minutes, 390 (M+H)$^+$.

EXAMPLE 6

Ethyl 6-oxo-3-phenoxy-7-phenyl-6,7-dihydrothieno[2,3-b]pyridine-2-carboxylate

A mixture of Intermediate 5 (500 mg, 1.32 mmol), phenol (137 mg, 1.46 mmol), Cu(II)O (209 mg, 1.46 mmol) and K$_2$CO$_3$ (221 mg, 1.60 mmol) in pyridine (100 ml) was heated at 115° C. for 18 h. The reaction was cooled to r.t., 2M HCl(aq) (30 ml) added and the aqueous extracted with EtOAc (3×20 ml). The combined EtOAc extracts were washed with 2M HCl(aq), brine, dried (MgSO$_4$) and concentrated in vacuo. The crude product was purified by chromatography on silica (0-10% EtOAc in DCM) to give the title compound as a solid (110 mg). $\delta_H$ (CDCl$_3$) 7.61-7.43 (3H, m), 7.42-7.29 (3H, m), 7.28-7.18 (2H, m), 7.00 (1H, t, J 7.4 Hz), 6.92 (2H, d, J 7.8 Hz), 6.49 (1H, d, J 9.6 Hz), 4.08 (2H, q, J 7.1 Hz), 1.04 (3H, t, J 7.1 Hz). LCMS (ES$^+$) RT 3.81 minutes, 392 (M+H)$^+$.

EXAMPLE 7

Ethyl 6-oxo-7-phenyl-3-(phenylthio)-6,7-dihydrothieno[2,3-b]pyridine-2-carboxylate A mixture of Intermediate 5 (500 mg, 1.32 mmol), benzenethiol (0.15 ml, 1.46 mmol) and K$_2$CO$_3$ (221 mg, 1.60 mmol) in DMF (10 ml) was heated at 80° C. under nitrogen for 18 h. The reaction was cooled to r.t., diluted with water and the aqueous extracted with EtOAc (3×20 ml). The combined EtOAc extracts were washed with water and brine, dried (MgSO$_4$) and concentrated in vacuo. The crude product was purified by chromatography on silica (0-5% EtOAc in DCM) to give the title compound as a solid (150 mg). $\delta_H$ (CDCl$_3$) 7.58-7.48 (3H, m), 7.46 (1H, d, J 9.7 Hz), 7.36-7.29 (2H, m), 7.25-7.07 (5H, m), 6.44 (1H, d, J 9.7 Hz), 4.21 (2H, q, J 7.1 Hz), 1.20 (3H, t, J 7.1 Hz). LCMS (ES$^+$) RT 3.97 minutes, 408 (M+H)$^+$.

EXAMPLE 8

Ethyl 6-oxo-7-phenyl-3-[(pyridin-2-ylmethyl amino]-6,7-dihydrothieno[2,3-b]pyridine-2-carboxylate From Intermediate 5 and 2-(aminomethyl)pyridine by the method of Example 1. White solid. $\delta_H$ (CDCl$_3$) 8.61 (1H, dq, J 0.8, 4.9 Hz), 8.21 (1H, br s), 7.81 (1H, d, J 9.8 Hz), 7.70 (1H, t, J 7.2 Hz), 7.54-7.45 (3H, m), 7.40 (1H, d, J 7.5 Hz), 7.28 (2H, m), 7.25 (1H, t, J 7.2 Hz), 6.39 (1H, d, J 9.8 Hz), 4.94 (2H, s), 4.18 (2H, q, J 7.2 Hz), 1.22 (3H, t, J 7.2 Hz). LCMS (ES$^+$) RT 3.32 minutes, 406 (M+H)$^+$.

EXAMPLE 9

3-(Benzylamino)-6-oxo-7-phenyl-6,7-dihydrothieno[2,3-b]pyridine-2-carbonitrile

A mixture of tris(dibenzylideneacetone)dipalladium(0) (14 mg, 0.015 mmol, 5 mol %), Intermediate 9 (100 mg, 0.30 mmol), caesium carbonate (137 mg, 0.42 mmol), benzylamine (0.039 ml, 0.36 mmol) and BINAP (19 mg, 0.03 mmol, 10 mol %) in anhydrous toluene (10 ml) was heated at reflux under nitrogen overnight. The mixture was partitioned between DCM and water. The organic phase was dried (Na$_2$SO$_4$) and concentrated in vacuo. Purification by column chromatography on silica (10% EtOAc in DCM) gave the title compound as a white solid. $\delta_H$ DMSO-d$_6$) 8.36 (1H, s), 8.03 (1H, d, J 9.7 Hz), 7.45-7.38 (3H, m), 7.31-7.29 (2H, m), 7.21-7.19 (4H, m), 7.18-7.08 (1H, m), 6.41 (1H, d, J 9.7 Hz), 4.54 (2H, s). LCMS (ES$^+$) RT 3.44 minutes, 358 (M+H)$^+$.

EXAMPLE 10

6-Oxo-7-phenyl-3-(phenylthio)-6,7-dihydrothieno[2,3-b]pyridine-2-carboxamide

A mixture of Intermediate 11 (300 mg, 0.86 mmol), K$_2$CO$_3$ (143 mg, 1.03 mmol) and benzenethiol (0.106 ml, 1.03 mmol) in DMF (15 ml) was heated at 100° C. for 8 h. The reaction was cooled to r.t., concentrated in vacuo and azeotroped with heptane (3×50 ml). The residue was partitioned between water/DCM and extracted with DCM (2×50 ml). The combined DCM extracts were dried (Na$_2$SO$_4$) and concentrated in vacuo. The crude product was triturated with EtOAc (2×20 ml) to give the title compound as an off-white solid (110 mg, 34%). $\delta_H$ (DMSO-d$_6$) 7.90-7.60 (2H, m), 7.50-7.30 (6H, m), 7.25-7.00 (5H, d, J 9.8 Hz), 6.3 (1H, d, J 9.6 Hz) LCMS (ES$^+$) RT 3.18 minutes, 379 (M+H)$^+$.

EXAMPLE 11

Ethyl 3-(benzoylamino)-6-oxo-7-phenol-6,7-dihydrothieno[2,3-b]pyridine-2-carboxylate Triethylamine (0.10 ml, 0.77 mmol), benzoyl chloride (0.10 ml, 0.77 mmol) and DMAP (20 mg) were added to a solution of Intermediate 8 (200 mg, 0.64 mmol) in DCM (5 ml). The reaction was stirred at room temperature for 18 h. The reaction was diluted with DCM (100 ml) and washed with brine. The organics were dried (MgSO$_4$) and concentrated in vacuo. The crude residue was purified by chromatography on silica (0-20% EtOAc in DCM) to give the title compound as a white solid (80 mg, 30%). $\delta_H$ (CDCl$_3$) 8.20 (1H, d, J 10.1 Hz), 8.01-7.98 (2H, m), 7.59-7.45 (6H, m), 7.37-7.31 (2H, m), 6.57 (1H, d, J 10.1 Hz), 4.22 (2H, q, J 7.1 Hz), 1.23 (3H, t, J 7.1 Hz). LCMS (ES$^+$) RT 3.74 minutes, 419 (M+H)$^+$.

EXAMPLE 12

Ethyl 6-oxo-7-henyl-3-[(phenylsulphonyl amino]-6,7-dihydrothieno[2,3-b]pyridine-2-carboxylate Sodium hydride (31 mg of a 60% suspension in mineral oil, 0.77 mmol) was added to a solution of Intermediate 8 (200 mg, 0.64 mmol) in DMF (5 ml). The solution was stirred at room temperature for 10 minutes before benzenesulphonyl chloride (0.10 ml, 0.77 mmol) was added and the reaction mixture then stirred for 18 h. The reaction mixture was poured into brine (50 ml) and extracted with chloroform (3×50 ml). The combined organic extracts were dried (MgSO$_4$) and concentrated in vacuo. The crude residue was purified by chromatography on silica (0-20% EtOAc in DCM) to give the title compound as a white solid (60 mg, 21%). $\delta_H$ (CDCl$_3$) 8.75 (1H, br s), 8.25 (1H, d, J 9.8 Hz), 7.60-7.55 (2H, m), 7.51-7.45 (4H, m), 7.38-7.29 (4H, m), 6.64 (1H, d, J 9.8 Hz), 4.05 (2H, q, J 7.1 Hz), 1.05 (3H, t, J 7.1 Hz). LCMS (ES) RT 3.58 minutes, 455 (M+H)$^+$.

EXAMPLE 13

Ethyl 3-[(anilinocarbonyl amino]-6-oxo-7-phenyl-6,7-dihydrothieno[2,3-b]pyridine-2-carboxylate Phosgene (69 mg of a 20% solution in toluene, 0.7 mmol) was added to a solution of Intermediate 8 (200 mg, 0.64 mmol) in toluene (5 ml) and DCM (2 ml) at 0° C. and the reaction stirred for 10 minutes. Triethylamine (0.20 ml, 1.54 mmol) and aniline (65 mg, 0.7 mmol) were added and the reaction stirred at room temperature for 18 hours. The reaction was diluted with DCM (100 ml) and washed with brine (2×100 ml). The organics were dried (MgSO$_4$) and concentrated in vacuo. The crude residue was purified by chromatography on silica (0-20% EtOAc in DCM) to give the title compound as a white solid (152 mg, 55%). $\delta_H$ (DMSO-d$_6$) 9.80 (1H, br s), 9.25 (1H, br s), 7.98 (1H, d, J 9.7 Hz), 7.68-7.58 (3H, m), 7.55-7.49 (4H, m), 7.33 (2H, m), 7.03 (1H, m), 6.54 (1H, d, J 9.7 Hz), 4.23 (2H, q, J 7.1 Hz), 1.22 (3H, t, J 7.1 Hz). LCMS (ES$^+$) RT 3.54 minutes, 434 (M+H)$^+$.

EXAMPLE 14

Ethyl 6-oxo-7-henyl-3-(2-phenylethyl)-6,7-dihydrothieno[2,3-b]pyridine-2-carboxylate Intermediate 12 (300 mg, 0.75 mmol) was dissolved in EtOAc (100 ml) and 10% palladium on carbon (50 mg) added. A hydrogen atmosphere was applied via balloon and the reaction stirred at room temperature for 18 h. The reaction mixture was filtered and the filtrate concentrated in vacuo. The crude residue was purified by chromatography on silica (10% EtOAc in hexanes) to give the title compound as a white solid (120 mg, 39%). $\delta_H$ (CDCl$_3$) 7.55-7.46 (4H, m), 7.34-7.31 (2H, m), 7.22-7.12 (5H, m), 6.52 (1H, d, J 9.7 Hz), 4.22 (2H, q, J 7.1 Hz), 3.32 (2H, m), 2.85 (2H, m), 1.25 (3H, t, J 7.1 Hz). LCMS (ES$^+$) RT 4.16 minutes, 404 (M+H)$^+$.

EXAMPLE 15

Ethyl 3-[hydroxy(phenyl)methyl]-6-oxo-7-phenyl-6,7-dihydrothieno[2,3-b]pyridine-2-carboxylate Intermediate 5 (1.134 g, 3.0 mmol) was dissolved in THF (50 ml) under a nitrogen atmosphere and cooled to between −105° C. and −111° C. n-BuLi (1.32 ml of a 2.5M solution in hexane, 3.3 mmol) was added dropwise. The reaction mixture was stirred for 30 mins at between −105° C. and −111° C. A solution of benzaldehyde (0.7 g, 6.6 mmol) in THF (5 ml) was added dropwise. The reaction mixture was allowed to warm to room temperature slowly and then poured into saturated NaHCO$_3$ solution (50 ml) and extracted with DCM (×2). The combined DCM extracts were dried (MgSO$_4$) and concentrated in vacuo. The crude product was purified by chromatography on silica (Et$_2$O) to give the title compound as an off-white solid (856 mg, 70%). $\delta_H$ (CDCl$_3$) 7.96 (1H, d, J 10 Hz), 7.52-7.70 (3H, m), 7.25-7.50 (7H, m), 6.69 (1H, s), 6.62 (1H, d, J 10 Hz), 4.29 (2H, q, J 7 Hz), 1.36 (3H, t, J 7 Hz). LCMS (ES$^+$) RT 3.56 minutes, 406 (M+H)$^+$.

EXAMPLE 16

Ethyl 3-[hydroxy(6-methylpyridin-2-yl)methyl]-6-oxo-7-phenyl-6,7 dihydrothieno[2-3-b]pyridine-2-carboxylate A solution of Intermediate 5 (5.0 g, 13.0 mmol) in THF (500 ml) was cooled to −110° C. under nitrogen and n-BuLi (6.4 ml of a 2.5M solution in hexanes, 16 mmol) was added slowly. A solution of 6-methyl-2-pyridinecarboxaldehyde (2.42 g, 20 mmol) in THF (5 ml) was added, the reaction mixture was warmed to −50° C. and NaHCO$_3$(aq) (500 ml) added. The mixture was extracted with DCM (3×100 ml). The combined organic extracts were dried (MgSO$_4$) and concentrated in vacuo. The crude product was purified by chromatography on silica (20% EtOAc in DCM) to give the title compound as a white solid (1.23 g, 42%). $\delta_H$ (CDCl$_3$) 7.82 (1H, d, J 9.8 Hz), 7.51-7.46 (4H, m), 7.29 (2H, br s), 7.02 (2H, t, J 7.0 Hz), 6.89 (1H, s), 6.41 (1H, d, J 9.8 Hz), 6.01 (1H, br s), 4.32-4.19 (2H, m), 2.57 (3H, s), 1.25 (3H, t, J 7.0 Hz). LCMS (ES$^+$) RT 2.87 minutes, 420.9 (M+H)$^+$.

EXAMPLE 17

Ethyl 3-[hydroxy(3-methylphenyl)methyl]-6-oxo-7-phenyl-6,7-dihydrothieno[2,3-b]pyridine-2-carboxylate From Intermediate 5 and 3-methylbenzaldehyde by the method of Example 16. Light tan solid. $\delta_H$ (CDCl$_3$) 7.86 (1H, d, J 9.8 Hz), 7.56-7.47 (3H, m), 7.33 (2H, d, J 7.1 Hz), 7.18-7.11 (4H, m), 7.02 (1H, d, J 7.1 Hz), 6.57 (1H, s), 6.53

(1H, d, J 9.8 Hz), 4.20 (2H, q, J 7.1 Hz), 2.28 (3H, s), 1.21 (3H, t, J 7.1 Hz). LCMS (ES+) RT 3.61 minutes, 420 (M+H)+.

EXAMPLE 18

3-[Hydroxy(phenyl)methyl]-6-oxo-7-phenyl-6,7-dihydrothieno[2,3-b]pyridine-2 carbonitrile Intermediate 9 (520 mg, 1.57 mmol) was dissolved in THF (30 ml) and cooled to −100° C. n-BuLi (2.5M in hexanes, 0.75 ml, 1.9 mmol) was added dropwise with the internal temperature kept below −95° C. The red solution was stirred at −100° C. for 30 min before the addition of a solution of benzaldehyde (0.24 ml, 2.4 mmol) in THF (10 ml). The reaction mixture was allowed to warm to room temperature before addition of water (50 ml). The aqueous layer was extracted with DCM (2×100 ml) and the combined organic extracts dried (MgSO$_4$) and concentrated in vacuo. The crude product was purified by chromatography on silica (10-20% EtOAc in DCM) to give the title compound as a white solid (140 mg, 25%). $\delta_H$ (CDCl$_3$) 7.90 (1H, d, J 9.8 Hz), 7.57-7.23 (10H, m), 6.52 (1H, d, J 9.8 Hz), 6.18 (1H, d, J 3.7 Hz), 2.89 (1H, br s). LCMS (ES+) RT 3.24 minutes, 359 (M+H)+.

EXAMPLE 19

3-[Hydroxy(3-methylphenyl)methyl]-6-oxo-7-phenyl-6,7-dihydrothieno[2,3-b]pyridine-2-carbonitrile From Intermediate 9 and 3-methylbenzaldehyde by the method of Example 18. White solid. $\delta_H$ (CDCl$_3$) 7.90 (1H, d, J 9.7 Hz), 7.55-7.45 (3H, m), 7.30-7.18 (5H, m), 7.05 (1H, m), 6.51 (1H, d, J 9.7 Hz), 6.13 (1H, d, J 3.2 Hz), 2.96 (1H, d, J 3.2 Hz), 2.11 (3H, s). LCMS (ES+) RT 3.38 minutes, 373 (M+H)+.

EXAMPLE 20

Ethyl 7-(cyclopropylmethyl)-3-[hydroxy(phenyl)methyl]-6-oxo-6,7-dihydrothieno[2,3-b]pyridine-2-carboxylate A solution of Intermediate 13 (1.0 g, 2.81 mmol) and benzaldehyde (0.45 ml, 4.22 mmol) in anhydrous THF (100 ml) under nitrogen was cooled to −78° C. tert-Butyllithium (3.47 ml, 1.7M in pentane, 5.9 mmol) was added dropwise and the red solution allowed to stir at −78° C. for one hour. The solution was allowed to warm to −10° C. before the reaction was quenched by the addition of 10% aqueous ammonium chloride solution (250 ml). The mixture was extracted with DCM (3×100 ml), the organics washed with brine (2×200 ml), then dried (MgSO$_4$) and filtered, and the solvents removed in vacuo. The crude residue was purified by chromatography on silica (0-15% EtOAc in DCM) to give the title compound as an off-white solid (452 mg, 42%). $\delta_H$ (CDCl$_3$) 7.77 (1H, d, J 9.7 Hz), 7.34-7.32 (2H, m), 7.28-7.22 (2H, m), 7.20-7.17 (1H, m), 6.57 (1H, d, J 8.1 Hz), 6.44 (1H, d, J 9.7 Hz), 4.63 (1H, d, J 8.1 Hz), 4.33-4.22 (2H, m), 3.97 (2H, d, J 7.2 Hz), 1.35-1.28 (1H, m), 1.31 (3H, t, J 7.1 Hz), 0.54-0.48 (4H, m). LCMS (ES+) RT 3.59 minutes, 384 (M+H)+.

EXAMPLE 21

Ethyl 3-(anilinosulfonyl)-6-oxo-7-phenyl-6,7-dihydrothieno[2,3-b]pyridine-2-carboxylate A solution of Intermediate 5 (1.0 g, 2.65 mmol), in anhydrous THF (100 ml) under nitrogen was cooled to −78° C. n-Butyllithium (1.16 ml, 2.5M in hexanes, 2.91 mmol) was added dropwise and the red solution allowed to stir at −78° C. for five minutes. Sulphur dioxide was bubbled through the reaction for 5 minutes at −78° C. and the reaction then allowed to warm to room temperature. The volatiles were removed in vacuo and the crude residue suspended in DCM (50 ml). N-Chloro-succinimide (425 mg, 3.18 mmol) was added and the reaction stirred at room temperature for two hours. Aniline (0.500 ml, 5.3 mmol), pyridine (2 ml) and DMAP (10 mg) were added and the reaction stirred for 18 hours. The reaction was diluted with DCM (150 ml) and washed with brine (3×200 ml). The organics were dried (MgSO$_4$), filtered and the solvents removed in vacuo. The crude residue was purified by chromatography on silica (0-20% EtOAc in DCM) to give the title compound as a white solid (320 mg, 27%). $\delta_H$ (CDCl$_3$) 8.65 (1H, br s), 8.44 (1H, d, J 10.0 Hz), 7.57-7.48 (3H, m), 7.30-7.25 (2H, m), 7.22-7.17 (2H, m), 7.12-7.06 (3H, m), 6.58 (1H, d, J 10.0 Hz), 4.33 (2H, q, J 7.1 Hz), 1.29 (3H, t, J 7.1 Hz). LCMS (ES+) RT 3.59 minutes, 455 (M+H)+.

EXAMPLE 22

Ethyl 3-[(3-methylphenyl)thio]-6-oxo-7-phenyl-6,7-dihydrothieno[2,3-b]pyridine-2-carboxylate m-Thiocresol (1.99 ml, 16 mmol) was added to a suspension of sodium hydride (690 mg, 60% in mineral oil, 17.24 mmol) in DMF (50 ml) at −10° C. and the mixture warmed to r.t. for 2 h. Intermediate 5 (5 g, 13.26 mmol) was added and the mixture stirred at r.t. for 2 h. The solvent was removed in vacuo and the residue azeotroped with heptane (3×100 ml). Water (150 ml) was added and the mixture extracted with DCM (3×100 ml). The combined DCM extracts were washed with brine, dried (MgSO$_4$) and concentrated in vacuo. Purification by column chromatography (silica, 100% DCM) gave the title compound as an off-white solid (4.2 g, 75%). $\delta_H$ (CDCl$_3$) 7.63-7.53 (4H, m), 7.45-7.42 (2H, m), 7.20-7.16 (2H, m), 7.10-7.03 (2H, m), 6.52 (1H, d, J 9.6 Hz), 4.30 (2H, q, J 7.1 Hz), 2.32 (3H, s), 1.29 (3H, t, J 7.1 Hz). LCMS (ES+) RT 4.11 minutes, 421.9 (M+H)+.

EXAMPLE 23

Ethel 3-[2-(4-methylphenol)hydrazino]-6-oxo-7-phenyl-6,7-dihydrothieno[2,3-b]pyridine-2-carboxylate A mixture of Intermediate 5 (1.0 g, 2.6 mmol), tris(dibenzylideneacetone)-dipalladium(0) (0.24 g, 0.26 mmol) and BINAP (0.32 g, 0.52 mmol) in toluene (10 ml) was stirred under a nitrogen atmosphere for 10 minutes. p-Tolylhydrazine hydrochloride (0.5 g, 3.17 mmol), Cs$_2$CO$_3$ (2.06 g, 6.3 mmol) and toluene (5 ml) were added. The mixture was heated at 110° C. overnight under a nitrogen atmosphere. The reaction was cooled to r.t., brine (50 ml) added and the aqueous extracted with EtOAc (2×50 ml). The combined EtOAc extracts were dried (MgSO$_4$) and concentrated in vacuo. The crude product was purified by chromatography on silica (0-10% EtOAc in DCM) to give the title compound as an orange solid (85 mg, 7.7%). $\delta_H$ (CDCl$_3$) 8.66 (1H, br s), 8.30 (1H, d, J 9.8 Hz), 7.55-7.32 (3H, m), 7.30 (2H, d, J 7.0 Hz), 7.02 (2H, d, J 8.2 Hz), 6.78 (2H, d, J 9.8 Hz), 6.37 (1H, d, J 9.8 Hz), 5.80 (1H, br s), 4.16 (2H, q, J 7.1 Hz), 2.22 (3H, s), 1.20 (3H, t, J 7.2 Hz). LCMS (ES$^+$) RT 3.88 minutes, 420 (M+H)$^+$.

EXAMPLE 24

Ethyl 3-[(3-chlorophenyl)(hydroxy)methyl]-6-oxo-7-phenyl-6,7-dihydrothieno[2,3-b]pyridine-2-carboxylate From Intermediate 5 (5.0 g, 13 mmol) and 3-chlorobenzaldehyde (1.7 ml, 15 mmol) by the method of Example 16 to give 1.8 g (40%) of the title compound. $\delta_H$ (d$_3$-MeOD) 8.02 (1H, d, J 9.7 Hz), 7.48-7.38 (3H, m), 7.31 (1H, s), 7.23-7.16 (3H, m), 7.10-7.00 (2H, m), 6.83 (1H, s), 6.29 (1H, d, J 9.7 Hz), 4.09 (2H, q, J 7.1 Hz), 1.07 (3H, t, J 7.1 Hz). LCMS (ES$^+$) RT 3.70 minutes, 440 (M+H)$^+$.

Biological Assays

The following assays and animal models can be used to demonstrate the potency and selectivity of the compounds according to the invention. In each assay an IC$_{50}$ value was determined for each test compound and represents the concentration of compound necessary to achieve 50% inhibition.

Preparation of Activated Human p38α for Inhibitor Assays

Purification of Human p38α

Human p38α, incorporating an N-terminal (His)6 tag, was expressed in baculovirus-infected High-Five™ cells (Invitrogen) according to the manufacturer's instructions. The cells were harvested 72 h post-infection and lysed in phosphate-buffered saline (PBS) containing 1% (w/v) β-octylglucoside and Complete, EDTA-free™ protease inhibitors (Roche Molecular Biochemicals). The lysate was centrifuged at 35000×g for 30 min at 4° C. and the supernatant applied to a NiNTA™ column (Qiagen). Bound protein was eluted by 150 mM imidazole in PBS (after a wash with 15 mM imidazole in PBS) and directly applied to a HiTrap Q™ column (AP Biotech). Bound protein was eluted using a 20 column volume, 0 to 1 M NaCl gradient. Fractions containing (His)6-p38 were aliquoted and stored at −70° C. prior to their activation.

Preparation of GST-MKK6EE-Containing Lysates

*E. coli* (BL21 pLysS) expressing the constitutively-activated form of human MKK6 fused with an N-terminal glutathione-5-transferase tag (GST-MKK6EE) were harvested by centrifugation and frozen at −70° C. Cells were lysed by resuspension in 1/10th the culture volume of PBS containing Complete, EDTA-free™ protease inhibitors followed by sonication on ice for 4×15 sec. Cell debris was removed by centrifugation at 35,000×g and the resultant supernatant stored in aliquots at −70° C.

Activation of (His)6-p38

0.45 ml of purified (His)6-p38 was incubated with 50 µl of the GST-MKK6EE-containing lysate for 30 min at 23° C. in the presence of 1 mM β-glycerophosphate, 10 mM MgCl$_2$ and 9 mM ATP. The extent of activation was monitored by mass spectrometric detection of the doubly-phosphorylated form of (His)6-p38, which routinely comprised greater than 90% of the final (His)6-p38 preparation. The activated (His) 6-p38 was then diluted×10 in PBS and repurified using the method described above. The concentration of purified, activated (His)6-p38 was measured by UV absorbance at 280 nm using A280, 0.1%=1.2 and the preparation stored in aliquots at −70° C. prior to its use in inhibitor assays.

p38 Inhibition Assays

Inhibition of Phosphorylation of Biotinylated Myelin Basic Protein (MBP)

The inhibition of p38-catalysed phosphorylation of biotinylated MBP is measured using a DELFIA-based format. The assay was performed in a buffer comprising 20 mM HEPES (pH 7.4), 5 mM MgCl$_2$ and 3 mM DTT. For a typical IC$_{50}$ determination, biotinylated MBP (2.5 µM was incubated at room temperature in a streptavidin-coated microtitre plate together with activated gst-p38 (10 nM) and ATP (1 µM) in the presence of a range of inhibitor concentrations (final concentration of DMSO is 2 percent). After fifteen minutes the reaction was terminated by the addition of EDTA (75 mM). The microtitre plate was then washed with Tris-buffered saline (TBS), prior to the addition of 100 µl of anti-phospho MBP antibody (mouse) together with europium-labeled anti-mouse IgG antibody. After one hour at room temperature the plate was again washed in TBS followed by the addition of Enhancement solution (PerkinElmer Wallac). Fluorescence measurements were performed after a further fifteen minutes at room temperature. IC$_{50}$ values are determined from the plot of log$_{10}$[inhibitor concentration] x-axis) versus percentage inhibition of the fluorescence generated by a control sample in the absence of inhibitor (y-axis).

Purification of Human Peripheral Blood Mononuclear Cells

Peripheral blood mononuclear cells (PBMC) were isolated from normal healthy volunteers. Whole blood was taken by venous puncture using heparinised vacutainers (Becton Dickinson), diluted 1 in 4 in RPMI 1640 (Gibco, UK) and centrifuged at 400×g for 35 min over a Ficoll-paque gradient (Amersham-Pharmacia Biotech, UK). Cells at the interface were removed and washed once followed by a low speed spin (250×g) to remove platelets. Cells were then resuspended in DMEM containing 10% FCS, penicillin 100 units ml$^{-1}$, streptomycin 50 µg ml$^{-1}$ and glutamine 2 mM (Gibco, UK).

Inhibitor Dilutions

Inhibitor stocks (20 mM) were kept as a frozen solution (−20° C.) in DMSO. Serial dilutions of inhibitors were performed in DMSO as 250-times concentrated stocks. Inhibitors were diluted 1 in 250 into tissue culture media, pre-warmed to 37° C. and transferred to plates containing PBMC. PBMC and inhibitors were incubated together for 30 min prior to addition of LPS. Inhibitors used in whole blood assays were prepared according to a different regime. Using the same stock solution serial dilutions of inhibitors were performed in DMSO. Inhibitors were then diluted 1 in 500 straight into whole blood in a volume of 1 µl. Inhibitor was incubated with whole blood for 30 min prior to the addition of LPS.

LPS Stimulation of PBMC

PBMC were resuspended at a density of 2×10$^5$ cells/well in flat-bottomed 96-well tissue culture treated plates. After the addition of inhibitor cells were stimulated with an optimal dose of LPS (*E. coli* strain B5:055, Sigma, at a final concentration of 1 µgml$^{-1}$) and incubated at 37° C. in 5% CO$_2$/95% air for 18 hours. TNF-α levels were measured from cell-free supernatants by sandwich ELISA BioSource #CHC1751).

LPS Stimulation of Whole Blood

Whole blood was taken by venous puncture using heparinised vacutainers (Becton Dickinson), and 500 µl of blood aliquoted into each well of a 24-well tissue culture treated plate. After the addition of inhibitor cells were stimulated with an optimal dose of LPS (*E. coli* strain B5:055, Sigma, at a final concentration of 1 μgml$^{-1}$) and incubated at 37° C. without $CO_2$ for 18 hours. TNF-α levels were measured from cell-free supernatants by sandwich ELISA (BioSource #CHC1751).

Rat LPS-Induced TNF Release

Male Lewis rats (180-200 g) are anaesthetised with Isofluor and injected i.v. with LPS* in a volume of 0.5 ml sterile saline. After 90 minutes blood is collected into EDTA tubes for preparation of plasma samples. Plasma is stored at −70° C. prior to assay for TNF-α by commercial ELISA.

Rat CIA

Female Lewis rats (180-200 g) are anaesthetised with Isofluor and immunised i.d. at the base of the tail with 2×100 μl of emulsion containing 4 mg/ml bovine collagen II in 0.01 M acetic acid and Freund's Incomplete Adjuvant at a ratio of 1:1. A polyarthritis develops with onset from about 13 days post-sensitisation. The disease is mainly confined to the ankles and is quantified by plethysmometry. Results are expressed as change in paw volume over time.

CONCLUSION

In the p38 inhibitor assays described above, the compounds of the Examples have $IC_{50}$ values of around 1 μM and below. The compounds of the invention are clearly potent inhibitors of p38 kinase, especially p38α kinase.

The invention claimed is:

1. A compound of formula (1):

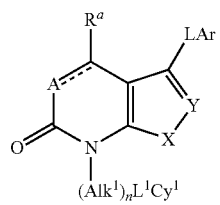

(1)

wherein
the dashed line joining A and C($R^a$) is present and represents a bond and A is a —C($R^b$)= group;
$R^a$ and $R^b$ are both hydrogen;
X is —S—;
Y is —C($R^{10}$)= in which $R^{10}$ is —$CONH_2$, —$CONHet^1$, —$CON(R^{12})Het^2$, —$CON(R^{12})Alk^5Het^2$ or —$CO_2Alk^6$ wherein —$NHet^1$ is pyrrolidinyl, imidazolidinyl, pyrazolidinyl, piperazinyl, morpholinyl, thiomorpholinyl, piperidinyl or thiazolidinyl, $R^{12}$ is a hydrogen atom or a straight or branched $C_{1-6}$ alkyl group, -$Het^2$ is cyclopentyl, cyclohexyl, pyrrolidinyl, imidazolidinyl, pyrazolidinyl, piperazinyl, morpholinyl, thiomorpholinyl, piperidinyl or thiazolidinyl, $Alk^5$ is a straight or branched $C_{1-6}$ alkylene, $C_{2-6}$ alkenylene or $C_{2-6}$ alkynylene chain, optionally interrupted by one, two or three —O— or —S— atoms or —S(O)—, —$S(O)_2$— or —N($R^{12}$)— groups, and $Alk^6$ is $C_{1-4}$ alkyl;
n is zero or the integer 1;
$Alk^1$ is an aliphatic or heteroaliphatic chain optionally substituted with one, two, three or more substituents where each substituent may be the same or different and is selected from halogen atoms, —OH, —$CO_2H$, —$CO_2R^4$ —$CO_2CH_3$, —$CON(CH_3)_3$, —$CONHR^4$, —CON($R^4$)$_2$, —$COR^4$, $C_{1-6}$ alkoxy, halo($C_{1-6}$)alkoxy, —SH, —S(O)$R^4$, —S(O)$_2R^4$, $C_{1-6}$ alkylthio, $NHR^4$, and —N($R^4$)$_2$, where $R^4$ is an optionally substituted straight or branched $C_{1-6}$ alkyl group, and such that where two $R^4$ groups are present they may be the same or different and, if attached to an N atom may be joined, together with the N atom to which they are attached, to form a heterocyclic ring, which heterocyclic ring may be optionally interrupted by a further heteroatom or heteroatom-containing group selected from —O—, —S—, —N($R^4$)—, —C(O)— or —C(S)—;
$L^1$ is a covalent bond or a linker atom or group, said linker atom or group being selected from —O—, —S—, —C(O)—, —C(O)O—, —OC(O)—, —C(S)—, —S(O)—, —S(O)$_2$—, —N($R^3$)—, —N($R^3$)O—, —N($R^3$)NH—, —CON($R^3$)—, —OC(O)N($R^3$)—, —CSN ($R^3$)—, —N($R^3$)CO—, —($R^3$)C(O)O—, —N($R^3$)CS—, —S(O)$_2$N ($R^3$)—, —N($R^3$)S(O)$_2$—, —N($R^3$)CON($R^3$)—, —N($R^3$)CSN($R^3$)— and —N($R^3$) $SO_2N(R^3)$—, where $R^3$ is a hydrogen atom or a straight or branched alkyl group, and such that where $L^1$ contains two $R^3$ groups these may be the same or different;
$Cy^1$ is a hydrogen atom or an optionally substituted cycloaliphatic, polycycloaliphatic, heterocycloaliphatic, polyheterocycloaliphatic, aromatic or heteroaromatic group, said optional substituent being selected from halogen, $C_{1-6}$ alkyl, halo($C_{1-6}$ alkyl), $C_{1-6}$ alkoxy, halo($C_{1-6}$ alkoxy), cyano, —$CO_2CH_3$, —$CO_2C$ ($CH_3$)$_3$, nitro, amino, —$NHCH_3$, —$N(CH_3)_2$, —$COCH_3$ and —$NHCOCH_3$;
L is an atom or chain —($CH_2$)$_p$Het($CH_2$)$_q$—;
p and q, which may be the same or different, are each zero or the integer 1;
Het is an —O— or —S— atom or a —C($R^{3a}$)($R^{3b}$)—, —C(O)—, —C(O)O—, —OC(O)—, —C(S)—, —S(O)—, —S(O)$_2$—, —N($R^{3c}$)O—, —N($R^{3c}$)NH—, —N($R^{3c}$)C($R^{3a}$)($R^{3b}$)—, —CON($R^{3c}$)—, —OC(O)N ($R^{3c}$)—, —CSN($R^{3c}$)—, —N($R^{3c}$)CO—, —N($R^{3c}$)C (O)O—, —N($R^{3c}$)CS—, —S(O)$_2$N($R^{3c}$)—, —N($R^{3c}$)S (O)$_2$—, —N($R^{3c}$)CON($R^{3d}$)—, —N($R^{3c}$)CSN($R^{3d}$)— or —N($R^{3c}$)S(O)$_2$N($R^{3d}$)— group and, when one or both of p and q is the integer 1, Het is additionally a —N($R^{3c}$)— group;
$R^{3a}$ and $R^{3b}$ are each independently a hydrogen atom, —OH, or an optionally substituted $C_{1-6}$ alkyl group;
$R^{3c}$ and $R^{3d}$ are each independently a hydrogen atom or a straight or branched alkyl group;
Ar is an optionally substituted aromatic or heteroaromatic group;
or a pharmaceutically acceptable salt thereof.

2. A compound as claimed in claim 1 wherein Y is —C($R^{10}$)= in which $R^{10}$ is —$CONH_2$ or —$CO_2Alk^6$ and $Alk^6$ is $C_{1-4}$ alkyl.

3. A compound as claimed in claim 1 wherein $Cy^1$ is phenyl or cyclopropyl.

4. A compound as claimed in claim 1 wherein Ar represents phenyl, halophenyl, dihalophenyl, ($C_{1-6}$ alkyl)phenyl, pyridinyl or ($C_{1-6}$ alkyl)pyridinyl.

5. A compound as claimed in claim 1 selected from
Ethyl 3-(benzylamino)-6-oxo-7-phenyl-6,7-dihydrothieno[2,3-b]pyridine-2-carboxylate;
Ethyl 3-(N-benzyl-N-methylamino)-6-oxo-7-phenyl-6,7-dihydrothieno[2,3-b]pyridine-2-carboxylate;
Ethyl 6-oxo-7-phenyl-3-[(1-phenylethyl)amino]-6,7-dihydrothieno[2,3-b]pyridine-2-carboxylate;
Ethyl 3-[(2,6-difluorobenzyl)amino]-6-oxo-7-phenyl-6,7-dihydrothieno[2,3-b]pyridine-2-carboxylate;

Ethyl 3-benzyl-6-oxo-7-phenyl-6,7-dihydrothieno[2,3-b]pyridine-2-carboxylate;

Ethyl 6-oxo-3-phenoxy-7-phenyl-6,7-dihydrothieno[2,3-b]pyridine-2-carboxylate;

Ethyl 6-oxo-7-phenyl-3-(phenylthio)-6,7-dihydrothieno[2,3-b]pyridine-2-carboxylate;

Ethyl 6-oxo-7-phenyl-3-[(pyridin-2-ylmethyl)amino]-6,7-dihydrothieno[2,3-b]pyridine-2-carboxylate;

6-Oxo-7-phenyl-3-(phenylthio)-6,7-dihydrothieno[2,3-b]pyridine-2-carboxamide;

Ethyl 3-(benzoylamino)-6-oxo-7-phenyl-6,7-dihydrothieno[2,3-b]pyridine-2-carboxylate;

Ethyl 6-oxo-7-phenyl-3-[(phenylsulphonyl)amino]-6,7-dihydrothieno[2,3-b]pyridine-2-carboxylate;

Ethyl 3-[(anilinocarbonyl)amino]-6-oxo-7-phenyl-6,7-dihydrothieno[2,3-b]pyridine-2-carboxylate;

Ethyl 6-oxo-7-phenyl-3-(2-phenylethyl)-6,7-dihydrothieno[2,3-b]pyridine-2-carboxylate;

Ethyl 3-[hydroxy(phenyl)methyl]-6-oxo-7-phenyl-6,7-dihydrothieno[2,3-b]pyridine-2-carboxylate;

Ethyl 3-[hydroxy(6-methylpyridin-2-yl)methyl]-6-oxo-7-phenyl-6,7-dihydrothieno[2,3-b]pyridine-2-carboxylate;

Ethyl 3-[hydroxy(3-methylphenyl)methyl]-6-oxo-7-phenyl-6,7-dihydrothieno[2,3-b]pyridine-2-carboxylate;

Ethyl 7-(cyclopropylmethyl)-3-[hydroxy(phenyl)methyl]-6-oxo-6,7-dihydrothieno[2,3-b]pyridine-2-carboxylate;

Ethyl 3-(anilinosulfonyl)-6-oxo-7-phenyl-6,7-dihydrothieno[2,3-b]pyridine-2-carboxylate;

Ethyl 3-[(3-methylphenyl)thio]-6-oxo-7-phenyl-6,7-dihydrothieno[2,3-b]pyridine-2-carboxylate;

Ethyl 3-[2-(4-methylphenyl)hydrazino]-6-oxo-7-phenyl-6,7-dihydrothieno[2,3-b]pyridine-2-carboxylate; and Ethyl 3-[(3-chlorophenyl)(hydroxy)methyl]-6-oxo-7-phenyl-6,7-dihydrothieno[2,3-b]pyridine-2-carboxylate.

6. A pharmaceutical composition comprising a compound of claim 1, or a pharmaceutically acceptable salt thereof, in association with a pharmaceutically acceptable carrier.

* * * * *